US011782038B2

(12) United States Patent
Mackey

(10) Patent No.: US 11,782,038 B2
(45) Date of Patent: Oct. 10, 2023

(54) MARITIME SULFUR DIOXIDE EMISSIONS CONTROL AREA FUEL SWITCH DETECTION SYSTEM

(71) Applicant: SeaArctos Holdings LLC, New York, NY (US)

(72) Inventor: Shannon Mackey, Ithaca, NY (US)

(73) Assignee: SEAARCTOS HOLDINGS, LLC, New York, NY (US)

( * ) Notice: Subject to any disclaimer, the term of this patent is extended or adjusted under 35 U.S.C. 154(b) by 820 days.

(21) Appl. No.: 16/836,173

(22) Filed: Mar. 31, 2020

(65) Prior Publication Data
US 2020/0309754 A1 Oct. 1, 2020

Related U.S. Application Data

(60) Provisional application No. 62/827,672, filed on Apr. 1, 2019.

(51) Int. Cl.
*G01N 33/00* (2006.01)
*B63B 79/10* (2020.01)
*G05B 19/042* (2006.01)
*F01N 11/00* (2006.01)
*G01M 15/10* (2006.01)
(Continued)

(52) U.S. Cl.
CPC ........ *G01N 33/0042* (2013.01); *B63B 79/10* (2020.01); *F01N 11/00* (2013.01); *G01M 15/102* (2013.01); *G05B 19/042* (2013.01); *G06F 16/27* (2019.01); *G06N 3/08* (2013.01); *G05B 2219/25255* (2013.01); *G05B 2219/25257* (2013.01); *Y02A 50/20* (2018.01)

(58) Field of Classification Search
CPC .. G01N 33/0042; B63B 79/10; G05B 19/042; G05B 2219/25255; G05B 2219/25257; G05B 19/0423; G06F 16/27; G06N 3/08; G06N 3/063; Y02A 50/20
USPC ........................................................ 73/114.71
See application file for complete search history.

(56) References Cited

U.S. PATENT DOCUMENTS

2001/0027070 A1* 10/2001 Morris ............... G01N 33/0073
440/89 R
2006/0236752 A1* 10/2006 Nakamura ......... G01N 33/0032
73/23.31
(Continued)

FOREIGN PATENT DOCUMENTS

| CN | 105865853 A * | 8/2016 | ........... G01N 1/2205 |
| CN | 205642942 U * | 10/2016 | ........... G01N 1/2205 |
| WO | WO-2023034857 A1 * | 3/2023 | ............. B63B 79/10 |

OTHER PUBLICATIONS

Translation CN-105865853-A, May 9, 2023 (Year: 2023).*
Translation CN-205642942-U, May 9, 2023 (Year: 2023).*

*Primary Examiner* — J. Todd Newton
(74) *Attorney, Agent, or Firm* — Brown & Michaels, PC

(57) ABSTRACT

A system for the maritime shipping industry to aid enforcement of the Sulfur Dioxide ($SO_2$) exhaust emissions regulations which uses neural networks and a novel sampling process to detect and record compliant operation of a ship regarding the fuel switching aspect of the regulation. The processing load of neural network training can be distributed over multiple identical self-contained, self-powered, self-communicating sensor units on each of the monitored ships.

20 Claims, 21 Drawing Sheets

(51) Int. Cl.
*G06N 3/08* (2023.01)
*G06F 16/27* (2019.01)

(56) References Cited

U.S. PATENT DOCUMENTS

| | | | | |
|---|---|---|---|---|
| 2009/0293646 | A1* | 12/2009 | Johnson | G01N 21/6486 |
| | | | | 73/863.22 |
| 2010/0206042 | A1* | 8/2010 | Johns | G01M 15/108 |
| | | | | 73/23.31 |
| 2010/0292934 | A1* | 11/2010 | Stark | G01M 15/106 |
| | | | | 702/47 |
| 2011/0146378 | A1* | 6/2011 | Brand | G01N 21/64 |
| | | | | 73/23.31 |
| 2012/0239308 | A1* | 9/2012 | Miller | G01N 1/2252 |
| | | | | 702/24 |
| 2016/0348561 | A1* | 12/2016 | Higashi | G01N 21/15 |
| 2018/0128798 | A1* | 5/2018 | Williamson | G01N 33/0024 |
| 2020/0309754 | A1* | 10/2020 | Mackey | G06F 16/27 |
| 2023/0009342 | A1* | 1/2023 | Koehl | F02C 6/203 |

* cited by examiner

MARITIME SULFUR DIOXIDE EMISSIONS CONTROL AREA FUEL SWITCH DETECTION SYSTEM

REFERENCE TO RELATED APPLICATIONS

This application claims one or more inventions which were disclosed in Provisional Application No. 62/827,672 filed Apr. 1, 2019, entitled "MARITIME SULFUR DIOXIDE EMISSIONS CONTROL AREA FUEL SWITCH DETECTION SYSTEM". The benefit under 35 USC § 119(e) of the United States provisional application is hereby claimed, and the aforementioned application is hereby incorporated herein by reference.

BACKGROUND OF THE INVENTION

Field of the Invention

The invention pertains to the field of environmental sensors. More particularly, the invention pertains to sensors and methods of using sensors to monitor emissions in a maritime application.

Description of Related Art

The maritime shipping industry is subject to the International Maritime Organization (IMO) regulations regarding Sulfur Dioxide ($SO_2$) exhaust emissions. The coast guards around the world, tasked with enforcing these regulations, have few options to detect non-compliance. Those that exist are expensive, and provide only very limited coverage. The US Coast Guard (USCG) and British Marine and Coastguard Agency (MCA) Coast Guards, among others, have stated publicly that they have no effective means to monitor compliance, and desire a system to help them identify which ships need scrutiny. The regulations are scheduled to become more stringent on Jan. 1, 2020, which is fueling anxiety in the market.

$SO_x$ exhaust emissions, barring any mitigation process such as exhaust gas cleaning systems, correlate directly to the sulfur content in the fuel. Effectively, the fuel sulfur concentration becomes a proxy for the exhaust sulfur concentration, and the fuel switching regulations reflect this understanding.

The regulations require ships without exhaust gas cleaning systems to switch to a compliant fuel for the zone they are in, and that a record be kept of the compliant behavior. The laws require that ships burn different concentrations of low sulfur fuel inside and outside of $SO_2$ Emissions Control Area (SECA) zones, and that a log of the fuel switch events are kept for review during inspections. Confirming that a fuel switch actually did happen when the log stated that it did is a lengthy and imprecise process, upon which fines and incarceration are weighed against.

Various attempts at "sniffing" the air over ships to detect suspect ships, whether with drones, planes, or bridge mounted sensors has proven tenuous, of limited range, and often expensive.

Permanent ship-mounted sensors are globally effective. However, laboratory grade sensing devices accurate enough to match fuel testing are exceedingly expensive to install and maintain—an untenable situation for consideration as a mandatory application.

This situation leaves the Coast Guards of the world with no effective way to know where to focus their attention.

SUMMARY OF THE INVENTION

The apparatus and methods described herein comprise a system for the maritime shipping industry to aid enforcement of the Sulfur Dioxide ($SO_2$) exhaust emissions regulations. The approach, using neural networks and a novel sampling process, is able to detect and record compliant operation of a ship regarding the fuel switching aspect of the regulation. The system distributes the processing load of neural network training over multiple identical self-contained, self-powered, self-communicating sensor units on each of the monitored ships. Along with robust redundancy and blockchain secured sensor data integrity, this deployment strategy scales up to cover the global fleet without demanding a proportional amount of "cloud" computing resources. Additionally, identical sensor processing units reduce the cost of manufacture and support.

The apparatus of the embodiments of the present invention captures compliant fuel switch determination. Fuel testing and bunker delivery note (BDNs) are easy for inspectors to verify after the fact. But, no current methods of inspection provide a confident determination that a ship has switched between high and low sulfur fuels appropriately outside of all SECA boundaries. The system of the present invention provides corroborating third party evidence to support legal appeals against contentious allegations of violation that could result in fines and incarceration. The system is beneficial to the industry as a whole by being distributed to ships themselves in a cost effective manner. The system provides some defense for compliant ships' operation, while also valuable in aggregate, to enforcement agencies to allow them to focus their scrutiny on the unknown ships.

The system and apparatus of the present invention continually self-adjusts to compensate and recognize different situations. The system collects $SO_2$, $CO_2$, and other compensatory data and applies statistical methods to continually adjust sensitivity and thresholds for distributed neural network training on the sensor units themselves—and in the cloud as aggregated datasets of all sensors for each ship. While a ship is burning a particular fuel, a particular pattern will emerge in the set of $SO_2$ influenced sensor readings locally—and aggregated in the cloud. When a ship burns a different fuel, a recognizably different pattern will emerge. Neural networks are good at capturing and recognizing these patterns. Patterns are combined that information with location data to demonstrate that a ship switched fuels in a compliant manner.

The system and apparatus of the present invention has no single point of failure resiliency. Aggregating data from multiple identical units produces a most resilient system while also reducing cost through reduced complexity of design, testing, manufacturing, and support. Distributing system configuration and sensor data via a proven distributed version control system to allow each sensor unit to adjust to system state and fail-over gracefully to a secondary or tertiary server. With intelligence distributed over every sensor unit, there is no single point of failure. Each sensor unit handles the processing load for its own data, allowing the system to scale automatically as it grows without dramatically increasing the burden on cloud resources. Transmitting a voyage worth of data at one time, instead of continuously, allows tremendous compression and reduced costs over cellular transmission links. Each unit transmits only the result of their processed data as necessary, over satellite, to convey switch detection data to the aggregate processor in the cloud. Tamper evidence or unit failure look the same, and will be handled in the same way.

The system and apparatus of the present invention has simple, redundant, independent systems. Sensor devices of the present invention are a self-contained units that include redundant, independent power and communication systems. Powered by their own solar and thermal energy harvesting systems, and communicating via satellite and cellular links, these units require no integration or installation effort beyond clamping them to the exhaust pipe with a wrench. The clamps are designed to work on straight or curved pipes with a wide range of pipe wall thicknesses and diameters. They use International Maritime Organization (IMO) approved secondary retention methods on the clamping bolt, and provide points for lanyard connection during installation.

BRIEF DESCRIPTION OF THE DRAWING

FIG. 12a shows a front mounting option on a pair of stacks of a single funnel.
FIG. 12b shows outboard side installation on multiple stacks of a single funnel.
FIG. 12c shows mounting options on a curved exhaust stack.
FIG. 12d shows a back mounting option on a plurality of stacks of a single funnel.
FIG. 12e shows multiple funnels in which multiple stacks have sensors units installed.
FIG. 12f shows a cruise ship funnel with multiple exhaust stacks and mounting of a sensor unit.

DETAILED DESCRIPTION OF THE INVENTION

The apparatus and methods described herein can determine that the fuel switching aspect, the most difficult regulatory compliance to confirm, is actually executed correctly with respect to an $SO_2$ Emission Control Area (SECA) boundary. The sensor system can then be used to corroborate the mandated log entries by providing immutable third party verification that fuel switches occurred appropriately at the SECA boundaries. It cannot assure that the ship burns compliant fuel—that is still on the operator to know what they are putting in their tanks—but it will indicate irregular readings in cases where sulfur concentration is changing unexpectedly, such as the case of an unclean fuel system. This information is valuable for a ship's operator in the appeals process of enforcement actions, and to greatly reduce inspection effort by those charged with enforcement.

The system can detect when a ship switched fuels, and on a compliant ship, that will confirm their log entries. The sulfur concentration of the fuel is easily confirmed now with portable fuel testers.

Figure 1:
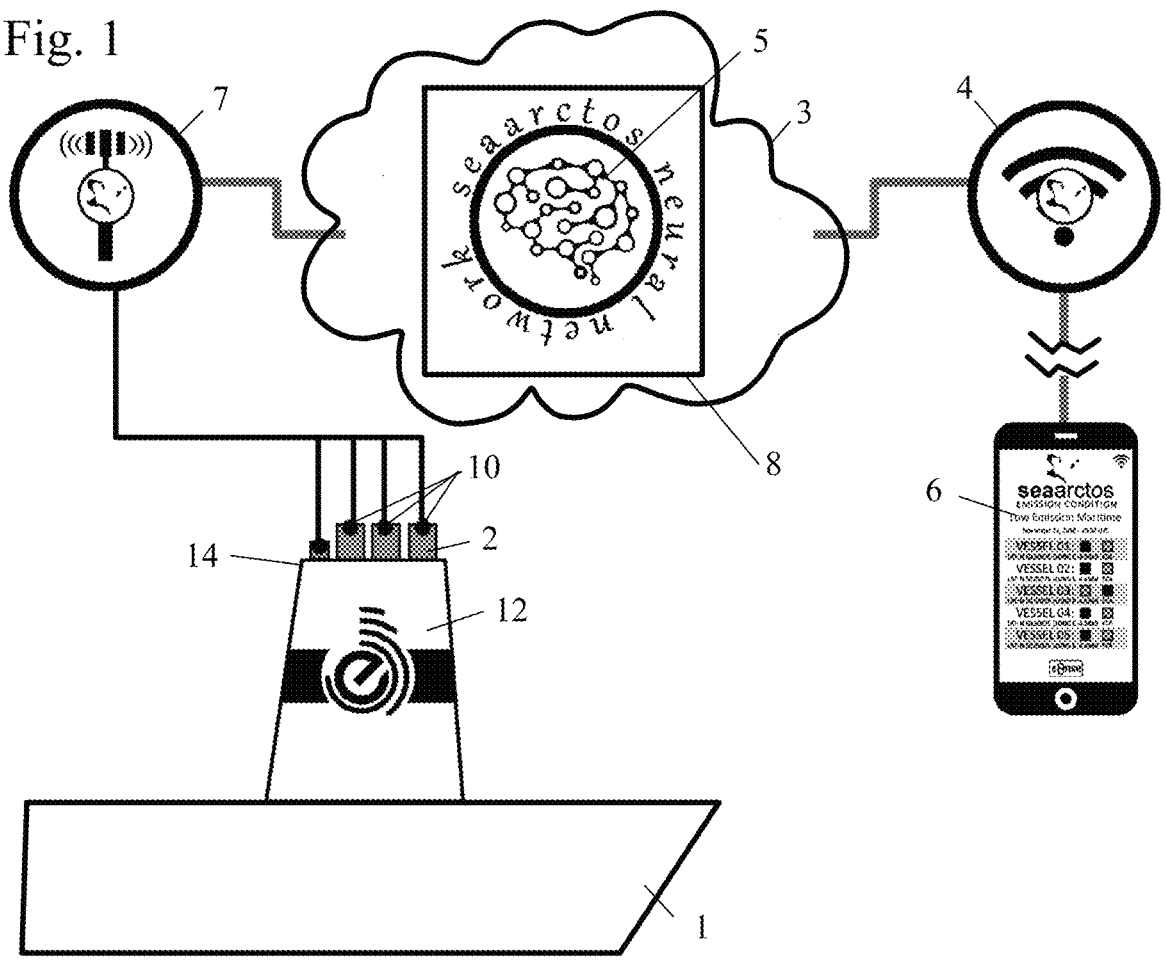
FIG. 1 shows a block overview of the system.

Referring to FIG. 1, at the top 14 of stack 12 on a ship 1, sensor units 10, on each exhaust pipe 2, sample actual vessel emissions, environment, location and operating parameters, which are immediately stored in an immutable blockchain secured record. Neural networks 5 are used to learn the signatures of compliant data as the ship 1 transitions over SECA zone boundaries in a compliant manner, thus allowing for outside and inside SECA comparative readings.

Distributing the bulk of the daily data processing load to the point of collection contributes to a globally scalable system that requires relatively few cloud resources to support.

The original voyage data, as well as the pre-processed results, are securely and redundantly replicated to the cloud 3 over cellular communications 7 as ships 1 approach ports and areas where enforcement actions are most likely to occur. The system also uses satellite alerts triggered by changes in vessel emissions.

Using the neural network 5, machine learning algorithms integrate the results from all of the sensor units 10 on a given ship 1 to further deduce failure, tampering, and irregularities that deserve investigation. Metadata regarding all of the pipes 2 and ships 1 is queried for fleetwide views, and can be further mined for value as the opportunity arises.

The cloud-based system, composed of well-proven open source database and distributed version control systems, supports the aggregation of the processed data from the sensor units 10. It is preferably designed to be deployed as multiple identical systems across differing cloud providers to protect from single points of failure and vendor lock-in.

Access to results is provided, preferably over standard secure web protocols 4, to support any web or mobile application 6. This data, while delivered directly to the client via subscription, can also be made available on a subscription basis to other interested parties. These can include, but are not limited to ports, states, managers, charterers, fuel and engine makers, coast guards, environmental protection agency (EPAs) and management system vendors.

To add clarity to the results from the sensor units 10, the system will preferably also log actual vessel events and correlate them to other data, enabling a generation of a large knowledge base of vessel events and how they affect sensor unit 10 readings.

Figure 2:
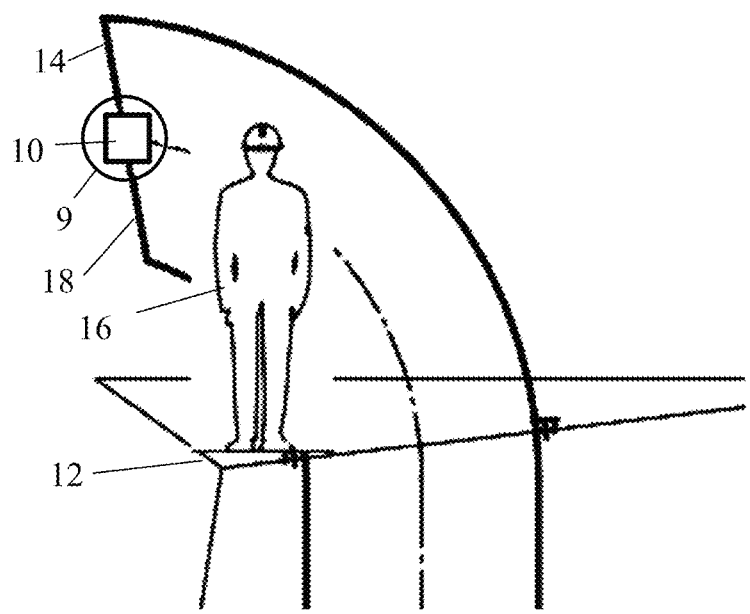
FIG. 2 shows a diagram of a representative mounting situation for the sensor units.

FIG. 2 shows a diagram of a representative mounting situation for the sensor units.

The easiest access to the gas that the sensors in the sensor unit 10 will be sensing is at the top 14 of the exhaust pipe 2 where no drilling, cutting or welding is necessary. This is, also, a place with practically the best solar exposure and a constant thermal differential from which to harvest energy. Furthermore, based on view of the sky from this point provides sufficient access for direct communications over available wireless links. This confluence of characteristics makes self-contained sensor units 10, with their own energy harvesting systems and data paths, an attractive solution. Additionally, by using multiple independent devices, single-point-of-failure is removed, allowing determination of single unit failure, degradation, or tampering.

The sensor unit 10 is mounted in a location roughly indicated by the circle 9 on a smoke stack 12 on a ship. Each stack 12 on a ship will have multiple exhaust pipes (not shown here) in one stack for all of the engines, generators, and boilers. On exhaust pipes that open straight up to the sky, the sensor unit 10 is mounted at a location on the outboard side 18 of the stack 12.

To install a sensor unit 10, an installer 16 stands on the stack 12, and clamps the sensor unit 10 on the outboard side 18 of the exhaust pipe to provide good access to Global Positioning System (GPS), satellite and cellular signals. Giving the installer 16 a common place 9 to install the unit 10 will ensure consistent orientation around which many other design decisions can be made—including the thermoelectric generator location, weep holes arrangement, and clamp style, which will be discussed in detail below.

Involvement of specialized trades and scheduling raise costs. Every decision was made to avoid requiring any integration with ship power or data infrastructure. This characteristic also results in simpler class testing. The installation of the sensor units 10 requires no special tools or skills to clamp the sensor unit 10 onto the edge of the exhaust pipe.

Sensors

While the independent energy and communications are foundational to an unprecedentedly economical compliance detection system, the application of auto-trained neural networks enable a novel sampling process using otherwise inadequate $SO_2$ sensors.

Detecting a fuel switch does not require highly accurate sensing devices, though it requires a number of additional sensor types. Any sensor unit that is responsive to just $SO_x$ concentrations is adequate.

However, the system might include some or all of these types of sensors:
  $SO_2$—sulfur dioxide sensors of no particular technology, simply ones that are proportionately responsive to concentration of $SO_2$ in exhaust gas.
  $CO_2$—carbon dioxide sensors of no particular technology, simply ones that are proportionately responsive to concentration of $CO_2$ in exhaust gas.
  Temperature—no particular precision, but temperature is known to affect $CO_2$ and $SO_2$ sensor readings.
  Humidity—no particular precision, but humidity is known to affect $CO_2$ and $SO_2$ sensor readings.
  Vibration—piezo or microphone, to convey engine or boiler activity. This is expected to correlate, and enhance the signal of, the $CO_2$ values in the neural network.
  Wind Direction/Speed—using a pressure sensor in the sample input tube. These values may indicate why there are variations in the gas reading, even if the engine and fuel has not been changed.
  Location—GPS—not affecting the gas sensor readings, but essential for using sample data to determine regulatory compliance.

There are additional sensors that collect internal system data for diagnostics and logistics. These values, while not specifically relevant to gas sensing, nonetheless impact the readings of the other sensors and readings could be integrated into the final result. These additional sensors may include, but are not limited to, one or more of the following:
  Supply Voltage—affects sensor values and sample pulse volume.
  Storage Voltage—used to determine if there is enough energy to complete various processes of sampling and data transmission.
  Thermoelectric Generator (TEG) temperature—determine if exhaust should be sampled, and detect thermoelectric generator failure.
  Thermal Energy Availability—current sensing for charge rate.
  Solar Energy Availability—current sensing for charge rate and daytime detection.
  Internal Temperature—to learn about thermal buildup and effectiveness of cooling strategies.
  Elevation/Speed/Direction—GPS—predict next sample time/location.

Data is processed locally and will also be collected for meta-analysis after upload to integrate into the data for all the sensor units 10 on a single ship or vessel.

Sampling

Incremental: The sampled gas is drawn in with a diaphragm pump with flexible membrane valves. Any type pump that can draw adequate vacuum in sub-milliliter increments, and have a very long life, is suitable. Characteristics of the very small and precise sample steps become additional inputs along with the sensor data.

Clearing: Pump tubes are arranged in a way to clear out the sample chamber afterward to increase the longevity of the $SO_2$ sensor element. The purge pump is connected, with a "T" fitting, into the exhaust intake line as well, so that that line can be cleared, and each new sample need not process stale sample gas. The purge pump also needs to capture and expel any condensation that may have occurred as the hot gasses cooled on their deliberately slow transit of the sample tubes.

Chamber: While working over a burning wick of very low sulfur "road" diesel fuel to try some different sample intake and purge routines while using a calibrated hand-held $SO_2$ sensor in a half pint size plastic container, it quickly became apparent that the sensor could hit its limits if the sample pump pulsed too long (~100 ms) or too quickly (~<2 seconds). It was not a surprise that these thresholds existed. But, the effect on the volume of the chamber prompted the relaxing of the design constraint that the sample chamber be as small as possible.

The small gas sample sense chamber that was originally designed proved too sensitive. Though, with a larger chamber, the purge times and power consumption becomes more of a concern. In any case, variations of the tubing length, chamber size, and orientation of the sensor in the chamber did, as expected, alter the response to the identical fuel. But, with those elements unchanging, the characteristics of the number of pulses of a certain duration (20-60 ms, depending on pump input voltage), with a fixed delay between pump pulses did produce similar values. This general repeatability, just with personally observed and manually recorded data provided a promisingly wide range that confidence remains high that there will be adequate "resolution" (a wide enough range of values before the sensor hits its limit) to automatically make distinctions between fuel types. Software/algorithm development continues to be able to automatically initialize the pulse size and delay values for the tubing and chamber volumes, and their response to the particular pipe that they are installed on, so that they continue to sample in a consistent manner providing values that span the range of the sensor itself.

Figure 3:
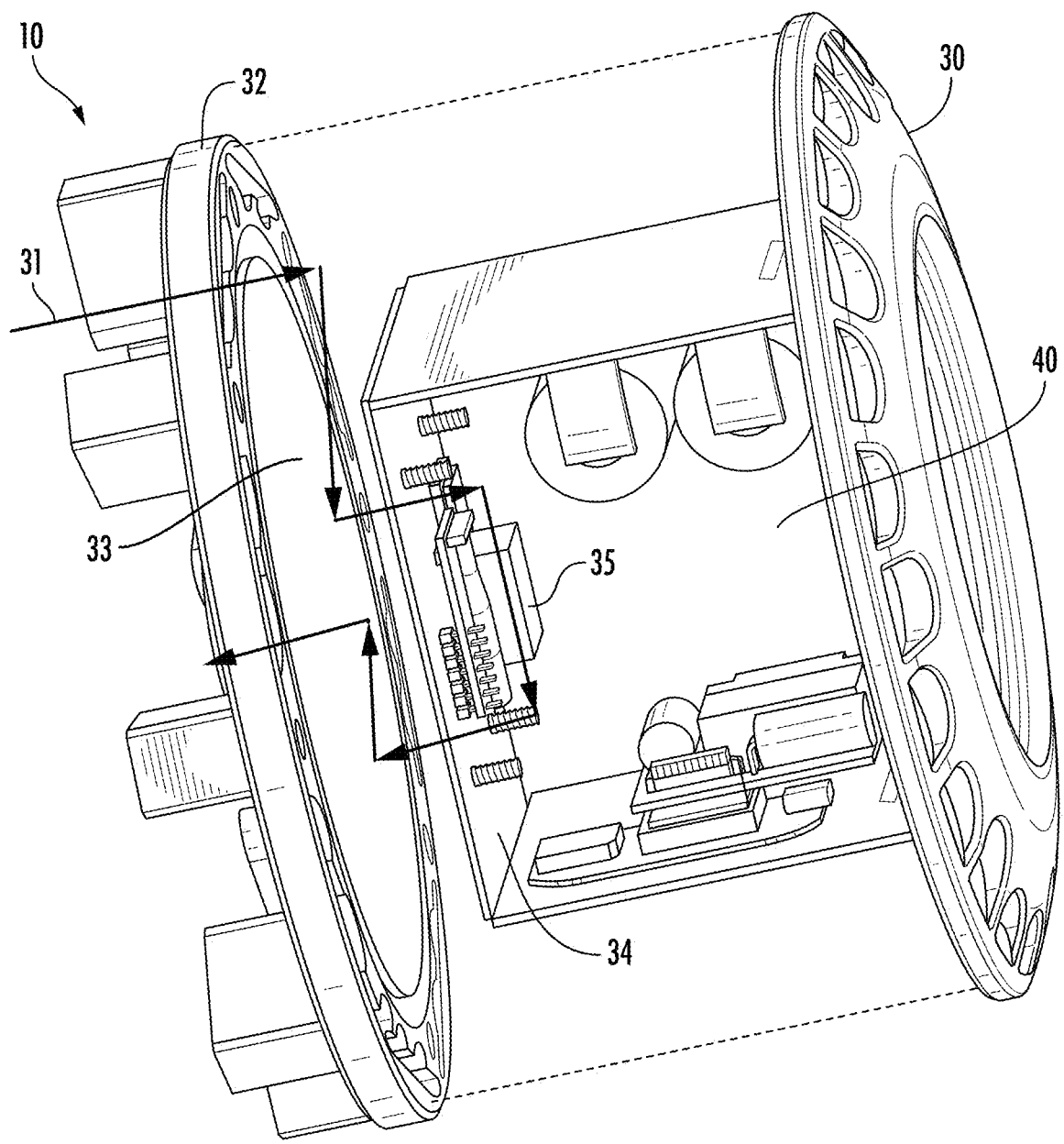
FIG. 3 shows a partial see-through view of a sensor unit.

Referring to FIG. 3, the pump block 33 fills the space between the sense chamber circuit board 34, on which sensor 35 is mounted, and the base 32 of the enclosure 30. It has an airtight seal between the base 32 and the circuit board 34, and moves the exhaust gas along the path indicated by arrows 31 to take a sample. The purge process moves the gas in the opposite direction, replacing the exhaust gas with fresh air.

Possible $SO_2$ sensors 35 which can be used for the system include the $SO_2$ Sulfur Dioxide Sensor 20 ppm Pinned Package made by SPEC Sensors of Newark, Calif. Other possible $SO_2$ sensors which might be used include the SO2-AE Sulphur Dioxide Sensor from Alphasense Ltd. of Great Notley, England, or the multiple-gas sensors from N5 Sensors, Inc., of Rockville, Md.

Figure 14:
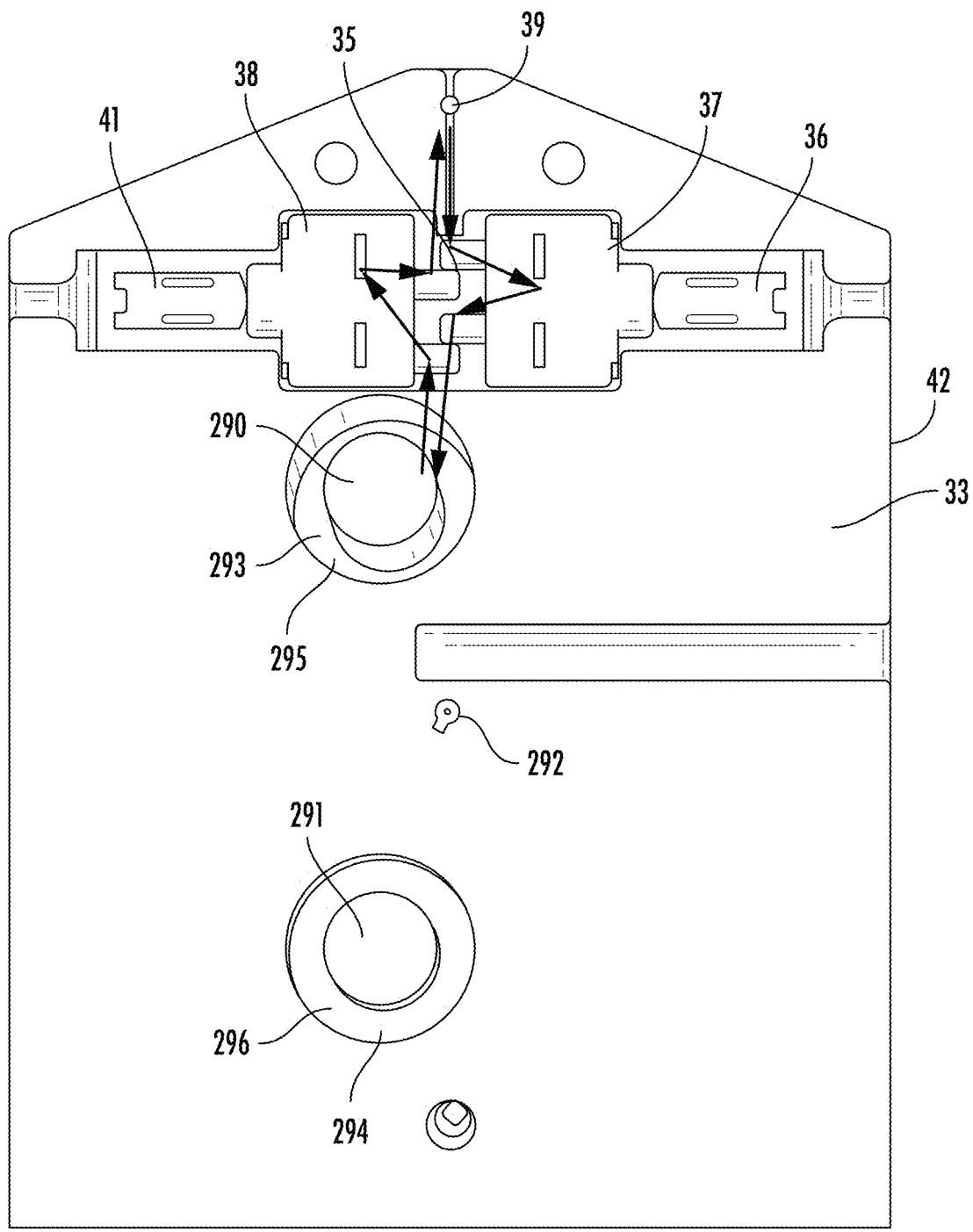
FIG. 14 shows a view of a sample pump/chamber system.

FIG. 14 shows a view of the pump block 33. Small electric pulses, onP the order of 15 milliseconds, drive the electric motor 36 of the sample pump 37 that will pull in about 3 ml of gas through hole 39, which connects to sample tubing leading from the exhaust stream. An important characteristic of the pump 37 is the need to be able to repeatably pull in very small gas samples. Peristaltic pumps are possible to use in this application, but may not be optimal for longevity concerns.

The pump 37 sends the sampled gas through an airstone filter 290 to the sensor 35. The gas returns from the sensor 35 through another airstone filter 291, then exits through hole 292.

A purge pump 38, driven by motor 41, can be used to force fresh air into the tubing and sense chamber 40 to reduce the exposure. In operation, fresh air would be drawn in through hole 292 and passed through airstone filter 291 into sensor chamber 40 with sensor 35. From the sensor chamber 40 with sensor 35, the air will pass through airstone filter 290 and the purge pump 38, then will exit through hole 39 into the sample tubing and out into the exhaust stream.

In the route of the gas through holes and channels, on either side of the sense chamber, the channel opens into a void wide enough to hold an "air stone" filter 290, 291, such that are used in aquarium fish tanks to distribute bubbles. These are intended to be a high surface area thermally conductive surface conducive to condensing moisture out of the gas that is pulled in from outside. The openings 293, 294 around the air stone filters 290, 291 serve as a reservoir for condensate until it weeps out of the tiny, capillary holes 295, 296 connected to outside of the housing to discharge the collected condensate.

Two pumps 37, 38 are entirely encapsulated inside their own tightly fitting openings in the block 33, and so arranged as to have their intake and output tube fittings matched up with the opposite tube fitting of the other pump in their own separate channel. Situated this way, and driving only one pump at a time, enables moving gas/air in opposite directions through the tubes formed by the holes and channels. One pump's output tube fitting is in the same channel as the opposite's input tube fitting, and in a separate channel as their own input tube fitting and the other's output tube fitting.

Processing

Figure 13:
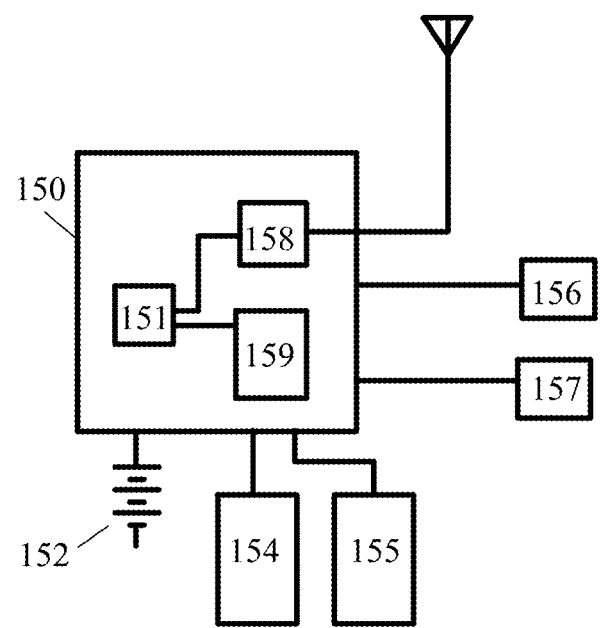
FIG. 13 shows a block diagram of the control and processing systems of the sensor unit.

FIG. 13 shows a block diagram of the control and processing systems of the sensor unit.

Controller 150: Microcontroller to control power, sampling 156, and sensors 157 and is the primary hardware interface.

Processor 151: Microprocessor to store sample data in a repository 159, manage neural network, and sync data over an available communications path 158.

Complimentary Energy Sources: Multiple energy harvesting sources is desirable regardless of the storage device. Solar 154 and thermoelectric 155 energy sources have complimentary characteristics. The solar charges relatively quickly and can provide enough power to run all the processes at the same time. Thermal, on the other hand, produces more slowly, but more continuously, particularly at a time that solar might have difficulty—in the constant cold night near the poles. While, in the heat near the equator, there is less temperature differential to produce power, but the sun always shines.

Solar 154: The PV modules are preferably sized such that they are adequate, under full sun, to run the process practically constantly.

Thermal Electric Generators 155: There are varying amounts of thermal energy available on the different diesel exhaust pipes, and at different times. Energy is harvested generally more slowly, but more constantly, than solar.

Management: There may be times when the energy sources will not harvest as fast as it is consumed by the sampling, processing, and radios. There are several different stages of processing that each have their own energy demands. By monitoring the amount of energy in storage, the Controller 150 will determine when there is adequate energy to start the Processor 151 to do any sort of work. The state of the process is always kept, and will be continued when adequate energy exists.

Figure 27:
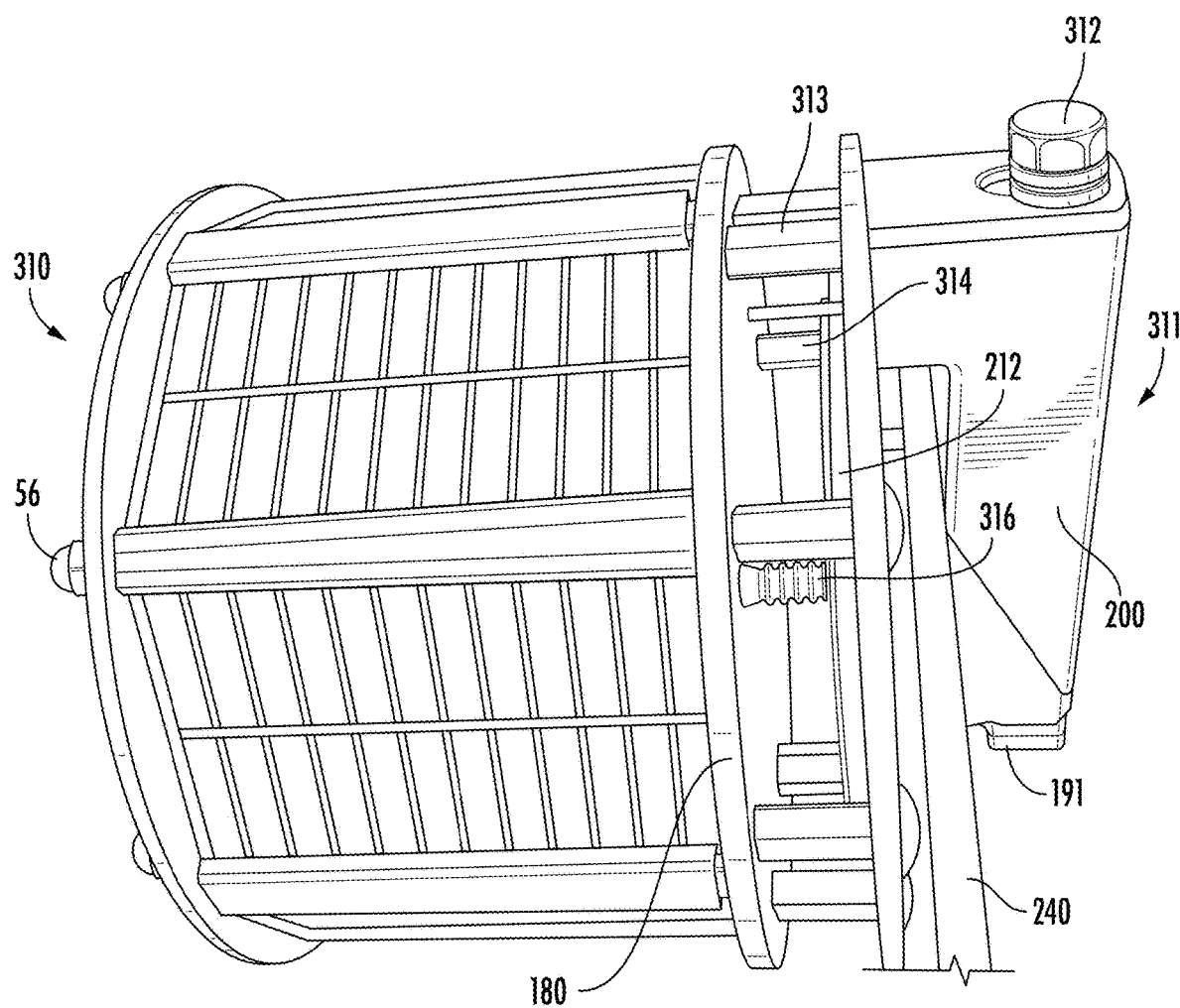
FIG. 27 shows a perspective view of an enclosure and clamp.

Referring to FIG. 27, an enclosure 310 is shown with a mounting clamp 311. The bolt 312 pulls the steel wedge 313 into the space between the sample tube 314 and the bracket 315 itself, which tightens very securely clamps onto a curved metal edge of an exhaust pipe.

The mounting clamp 311 also incorporates elements that beneficially affects the Exhaust Gas Sampling where an intake sample tube will draw in from inside the mounting clamp 311 structure where it hangs over the edge of the sample tube 314. The sample tube will not be in direct flow and exposure to soot, but will be drawing from the gas caught up in the mounting clamp 311 structure that reflects the relevant (not soot) gas components at the sampled time. This is further discussed relative to FIGS. 24-26.

The mounting clamp 311 must also incorporate means to allow installation without reaching over pipe or needing to see down in it. The mounting clamping 311 can handle a wide variation in thickness of pipe walls and keeps the TEG in solid contact with the pipe. A method to determine the exhaust pipe temperature will be valuable in understanding the efficacy of the situation for TEG usage on differing ships. It may also prove to be a useful determinate of engine activity. Alternately, by sensing the voltage and current supplied by the TEG, temperature may be determined from known values.

Additionally, a stainless steel filament pad may be used to fill the inside of a spring 316 that presses down on heat sink radiator 212 towards enclosure base 180, to further buffer the exhaust sample from weather. Here you see the gas sample tube 314 as it passes from enclosure base 180 through hole 214 (see FIG. 19). Wedge 313 works as spacers between the heat shield 210 and the enclosure base 180 to protect from heat.

Sensor Unit Enclosure Components

Figure 4:
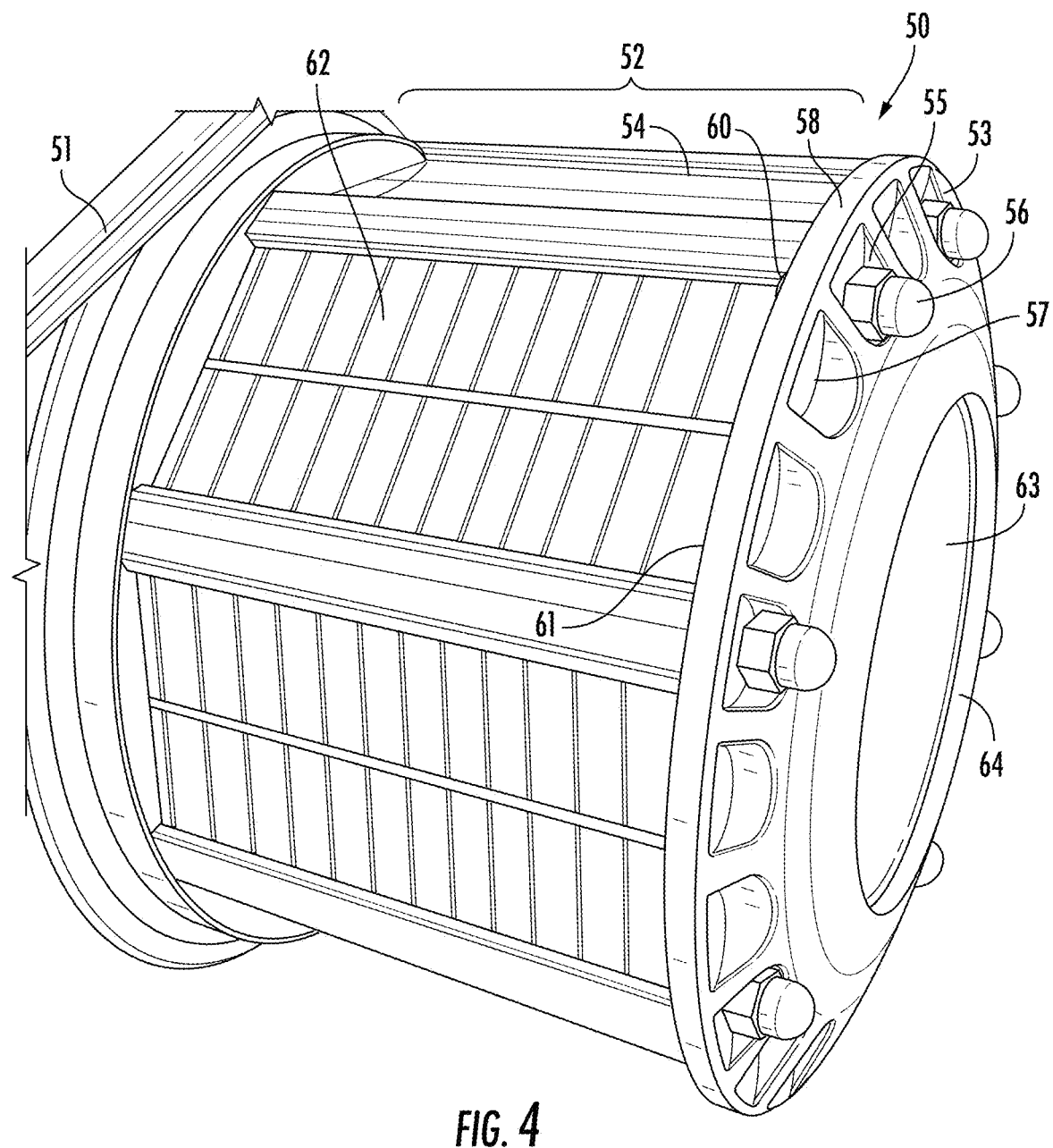
FIG. 4 shows a photograph of an enclosure.

Referring to FIG. 4, the outer housing 50 of the enclosure 31 consists of three components—a mounting base 51, a cylindrical middle 52 and a dome top 53. The pieces are fastened together, preferably bolted with common (inexpensive) length 6"×¼" stainless carriage bolts 54, washers 55 and cap nuts 56, through an array of equidistant holes 57 around the perimeter 58 of the top 53. These bolts 54 go through a thick steel plate, that is a primary structural member of the mounting clamp 311. The cap nuts 56 and the washers 55 aid in securing the dome top 53 to the enclosure 50, as the bolts 54 run through the entire cylindrical middle 52 of the outer housing 50.

The holes 57 fall just outside of the perimeter of a common (inexpensive) O-ring 60 that seals tight with compression from the bolts 54. The O-ring 60 is held captive in a groove 61 in the top wide enough to leave room for compression as the surfaces come together. There are slots and recesses in the three components to hold securely the edges of the PV modules 62. Below the PV modules 62 are channels for cooling airflow entering through openings/holes 57.

The dome top 53 holds one circular PV module 63 beneath an overhanging lip 64 that provides a surface for the silicone adhesive/sealant to press against.

The outer housing 50 needs to keep the electronics dry and, relatively, cool. A plastic, that can withstand the heat of the environment, is a possible material that can resist the corrosive environment. Heat shields will be required to keep the surface temperature from getting overly hot—even if the plastic can withstand the temperatures, the electronics inside will not. Most heat shields are rated for 80 C, but the $SO_2$ sensor itself prefers to be 40 C. The weather outside may well exceed 40 C, regardless of the proximity to the exhaust pipe. So, other passive means are used to shade and allow air flow to carry away heat as it is able.

The dome top 53 and mounting base 51 can be milled, while the circular middle piece 52 could be extruded. The middle piece 52 will also require drilling around the sides under each PV module 62.

The sensor units 10 are to be mounted on the outboard side of the pipes to give their antennae the best opportunity to communicate. Many ships or vessels have some or all the exhaust pipes curved toward the rear of the ship, which changes the mounting edge from horizontal to vertical. The circular design, with PV all around, can provide the same solar charging opportunity regardless of the pipe edge orientation.

Figure 5:
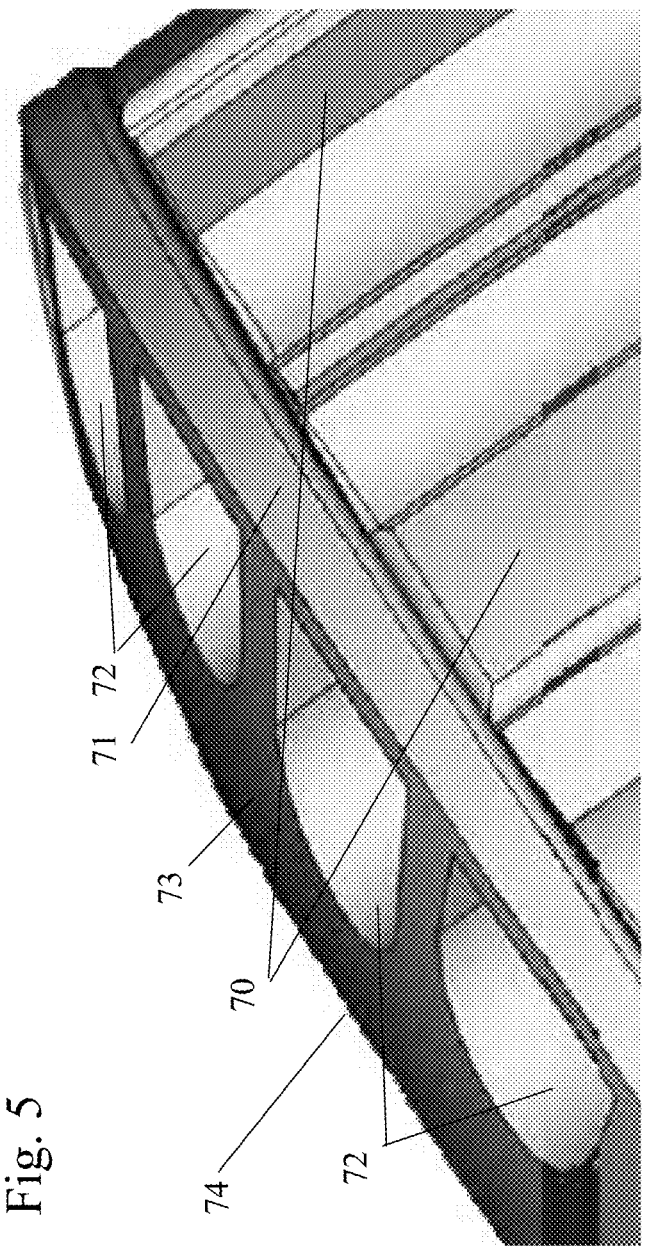
FIG. 5 shows a partial drawing of a photo-voltaic (PV) module.
Figure 6:
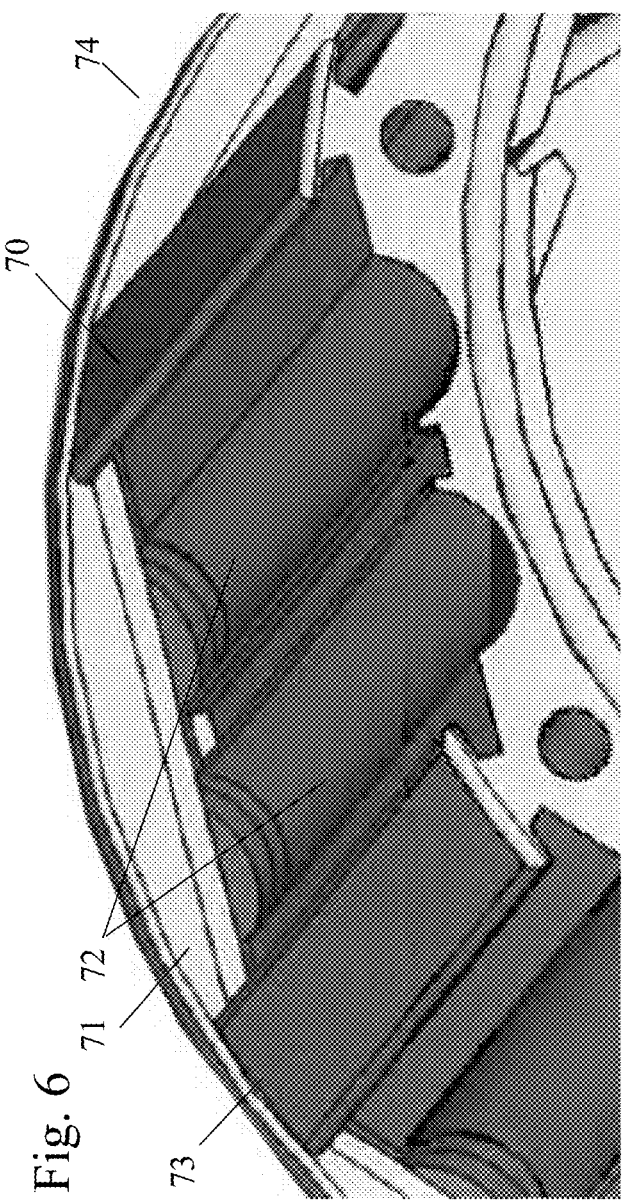
FIG. 6 shows a partial drawing of a PV module.

Referring to FIGS. 5 and 6, eight rectangular PV modules 70 surround the perimeter 71 effectively shade the surface by having little contact with the surface beneath and providing airflow channels 72 beneath. The channels 72 cut through the curving surface 73 of the dome 74 to aid the capture of wind from more directions than if they only came out of a flat surface. The channels 72 are retained by the PV modules 70.

Figure 7:
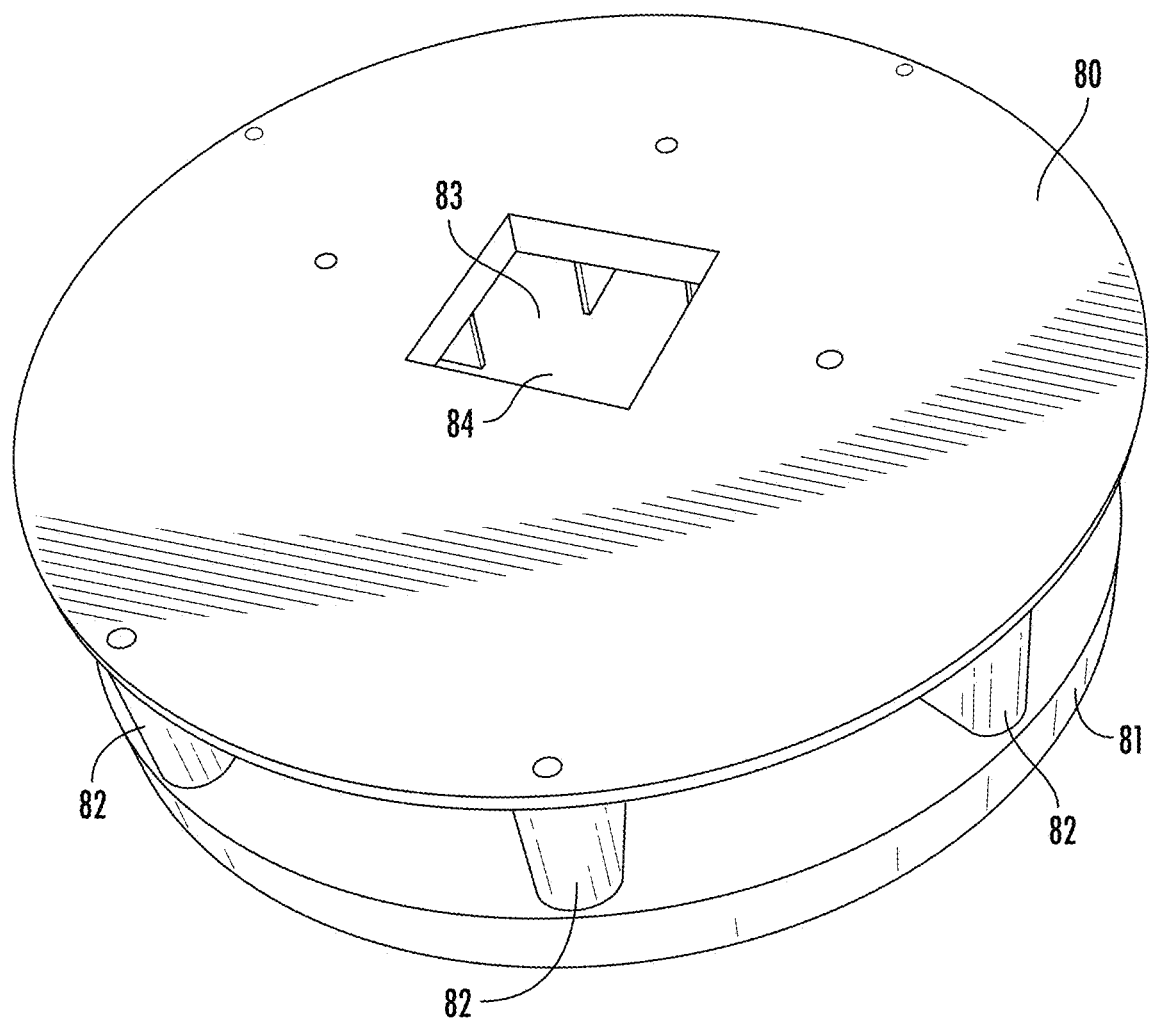
FIG. 7 shows a top perspective view of a thermoelectric generator (TEG).

Referring to FIG. 7, the mounting surface 80 is separated from the steel heat shields 81 by stand offs 82 or steel wedges 313 (FIG. 27) to allow ample cooling air flow. The shape of the stand-offs 82 direct air toward the center to optimize cooling the "cold" side 83 of the TEG 84. The stand-offs 82 are contiguous to the base plastic and contain channels for the various sampling tubes and the wires from the thermal electric module in the steel base. Running the penetrations into the enclosure through the length of the stand-offs provides more depth for sealing compounds to do their job properly. In this embodiment, the stand offs 82 serve as both standoff mounting feet and airflow fins to direct the air more directly through a heatsink mounting in "cold" side 83.

Figure 8:
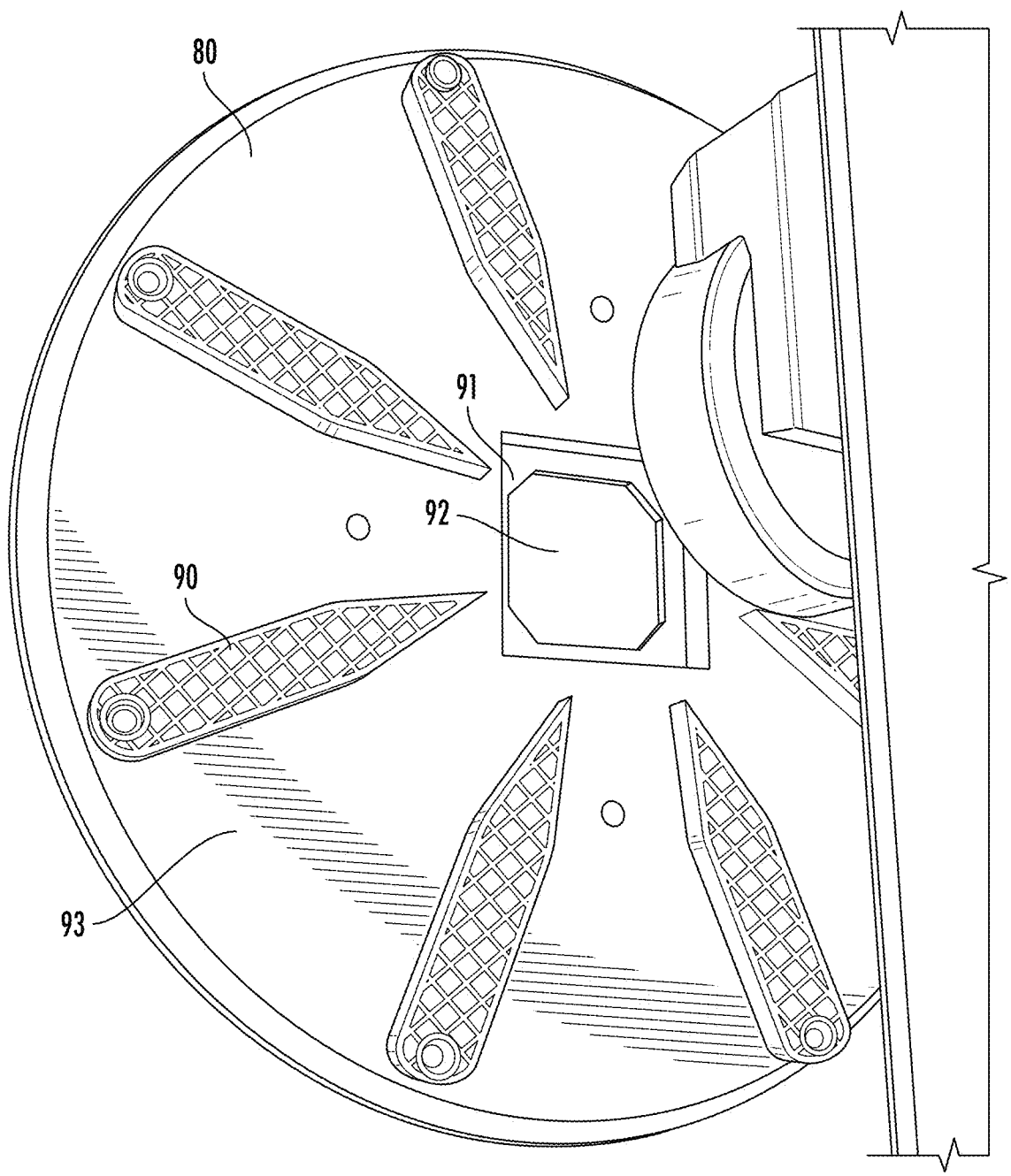
FIG. 8 shows an embodiment of a TEG.

FIG. 8 shows an embodiment with vent fins 90 directing wind over a heatsink 91 inside a square hole 92 in the base 93. Not visible in the figure, two diagonal notches route the TEG wires through holes in feet to the inside of the enclosure.

Figure 9:
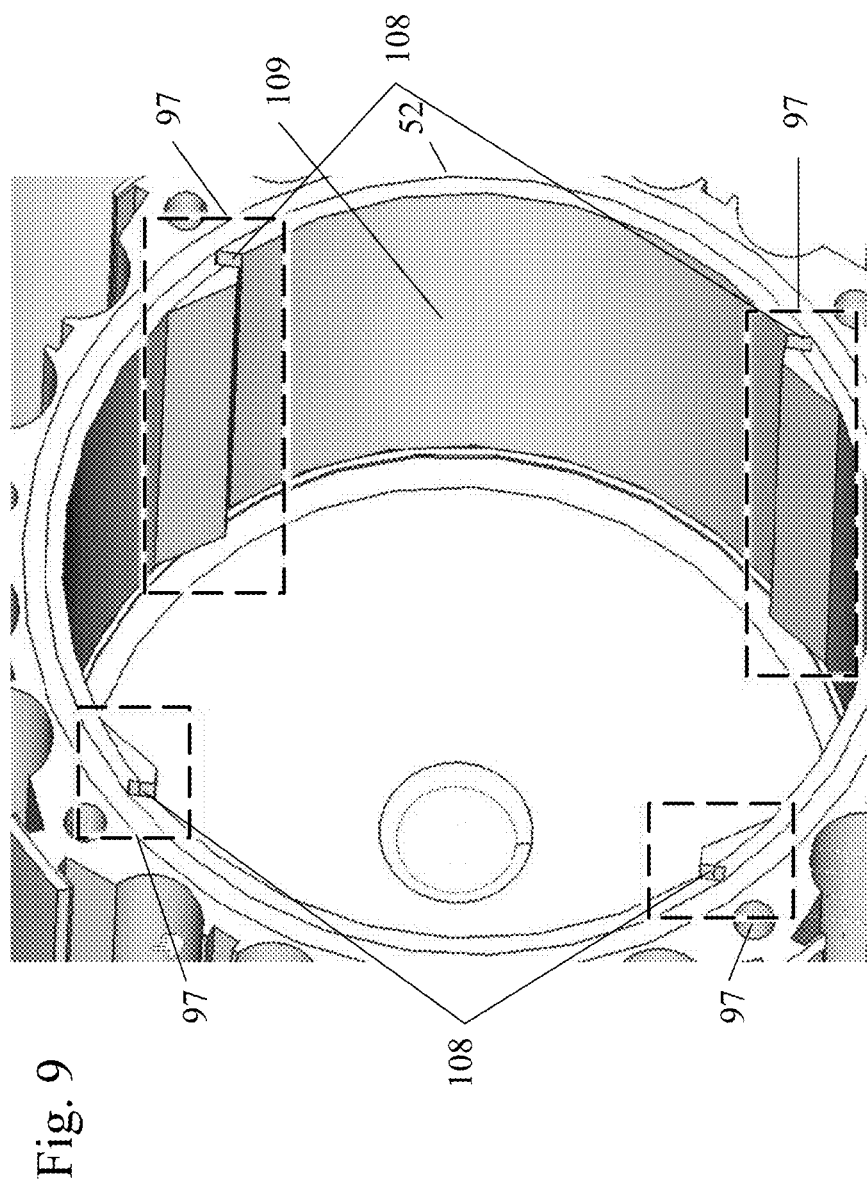
FIG. 9 shows a bottom view of an enclosure.

FIG. 9 shows the method of securing the printed circuit boards. There are slots 108 running the length, indicated by reference number 97, of the inside 109 of the cylindrical middle piece 52 providing a way to hold secure the circuit boards that are made to fit both the length and width provided.

Figure 28:
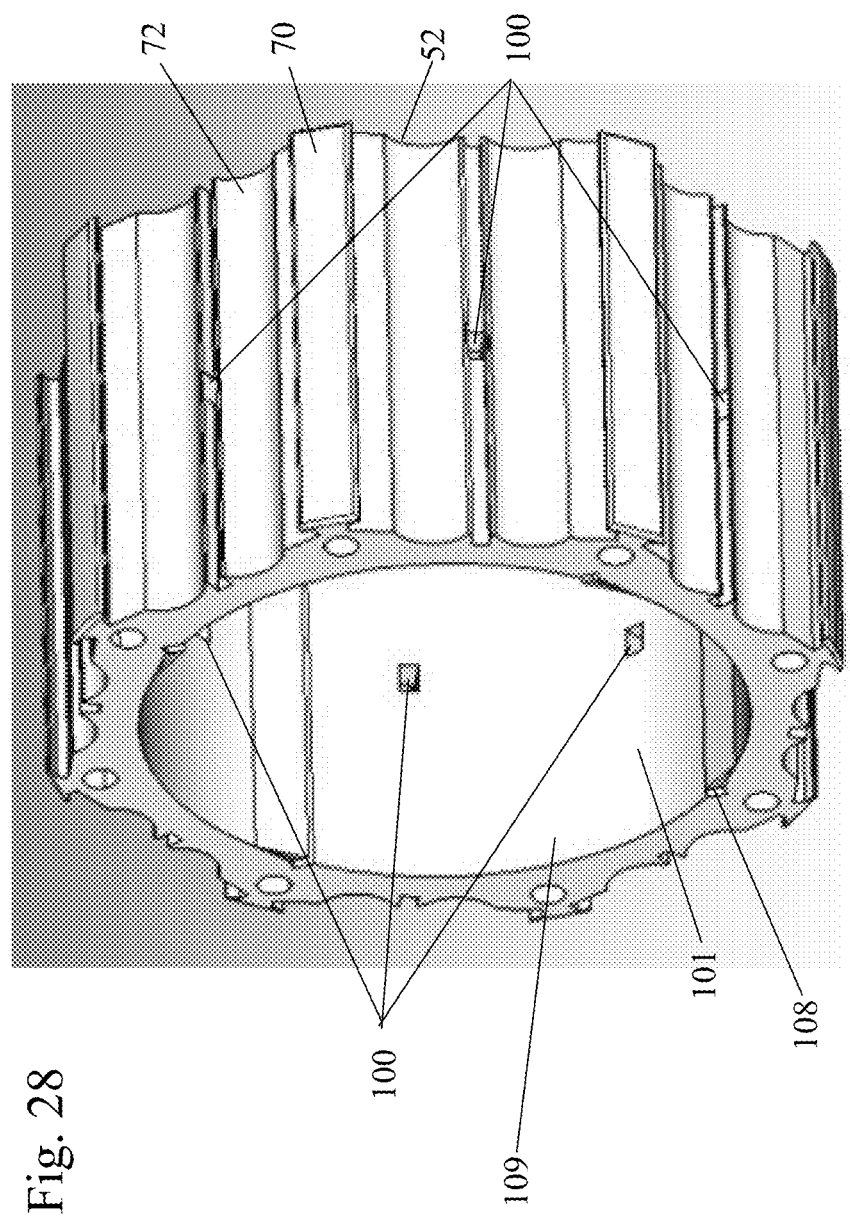
FIG. 28 shows a perspective view of a middle portion of an enclosure.

Referring to FIG. 28, the cylindrical middle piece 52 preferably provides weep holes 100 as a means to expel the moisture that will inevitably get into an enclosure by the expansion, contraction, and condensation caused by changing temperatures.

Behind the PV modules 70, between the channels 72, the cylindrical middle piece 52 touches a back to provide physical support, and a penetration for the wires to pass through. The location of that penetration, at the top of a ridge between channels 72, is a spot which has little chance of standing water exposure on the outside of enclosure. But, on the inside, any condensation will collect at the penetration on the bottom of the enclosure, and weep out through weep holes 100.

Figure 16:
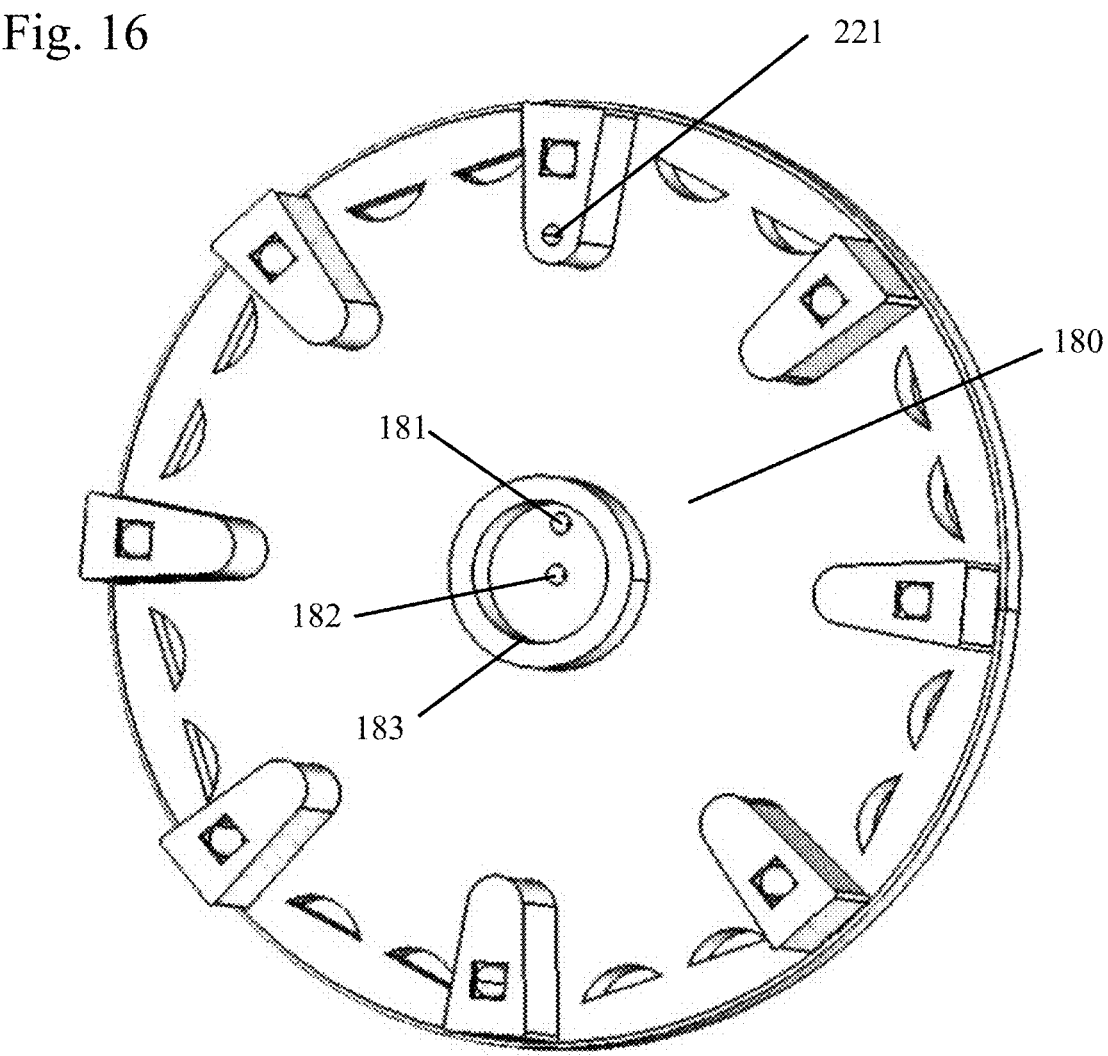
FIG. 16 shows an embodiment of a base bottom.

FIG. 16 shows a drawing of an enclosure base 180 with penetrations and heat sink press spring guide. Flange 183 has the dual purpose of holding a spring (not shown) centered between the enclosure base 180 and heat sink radiator 212. The spring presses the heat sink 91 down on the thermo-electric modules. Wires from the thermo-electric modules pass through hole 181 that is then sealed. Hole 182 is where the sampled gas exits after the sense chamber 40 and fresh air enters when purging the sense chamber 40.

Figure 17:
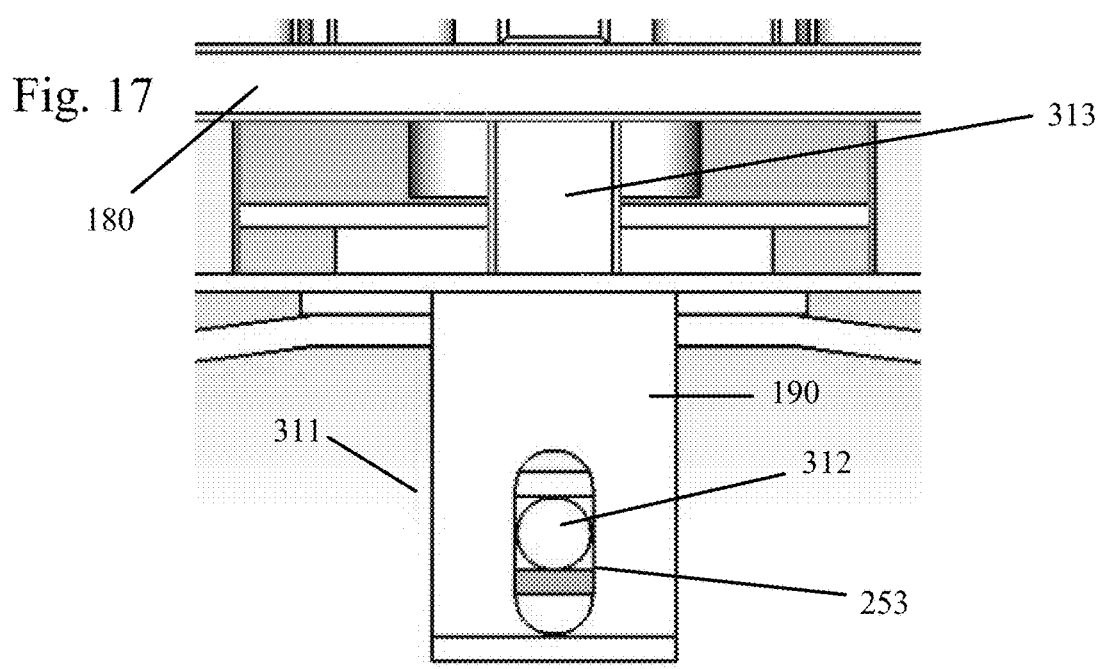
FIG. 17 shows a side-view detail of a base.
Figure 18:
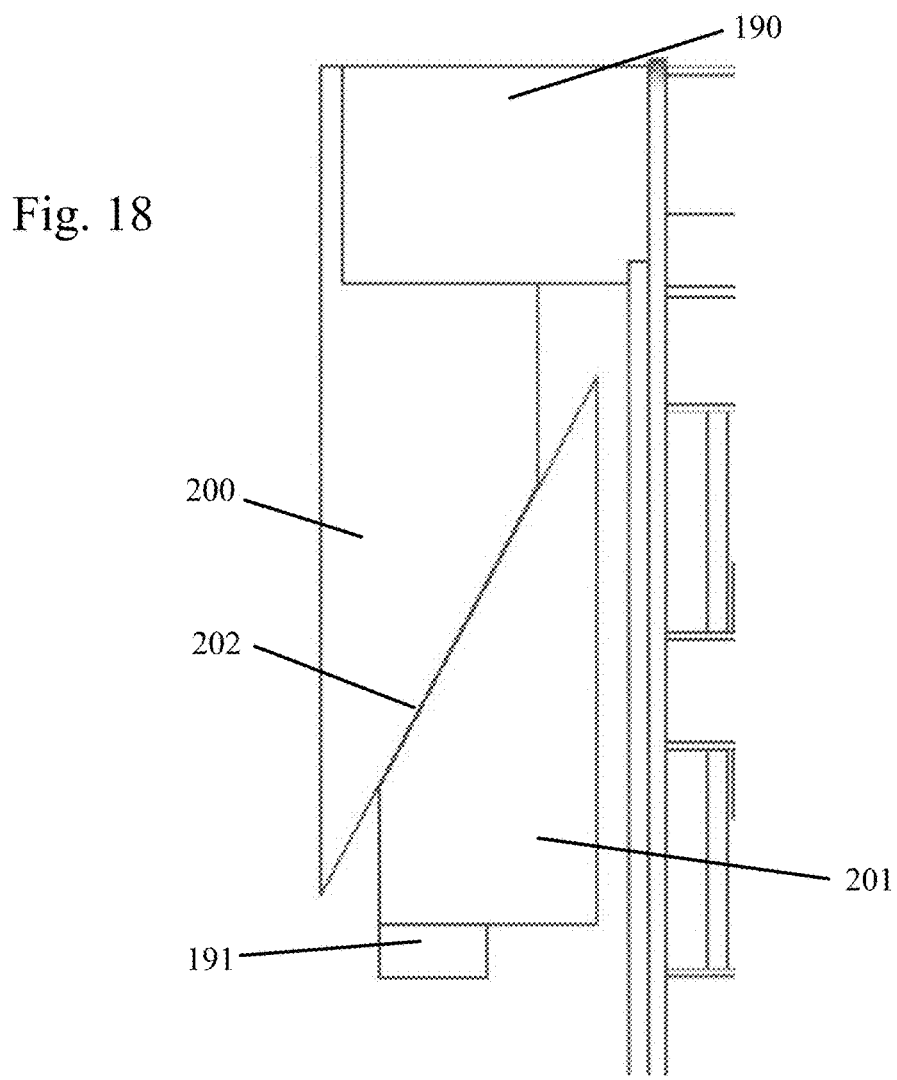
FIG. 18 shows a side-view detail of the clamp tube.

FIGS. 17-18 show a side-view detail of a base, showing how the bolt slides in a slot as the wedge is pulled tight by the bolt. FIG. 18 shows a side-view detail of the mounting clamp 311 attaching to a pipe. In this figure, a bolt 312 runs through the slot 253 in the top of clamp tube 190 and threads into the block 191 welded to the bottom of the wedge 201. Tightening the bolt 312 pulls the wedge 201 towards the rigid element 200. As the rigid element 200 and wedge 201 come together, the bearing edges 202 slide the wedge 201, and therefore the bolt 312 in the slot 253 in the top of clamp tube 190. Sliding wedge closes the gap between the wedge 201 and the rigid element 203 that will clamp, for example, the pipe edge metal.

Figure 19:
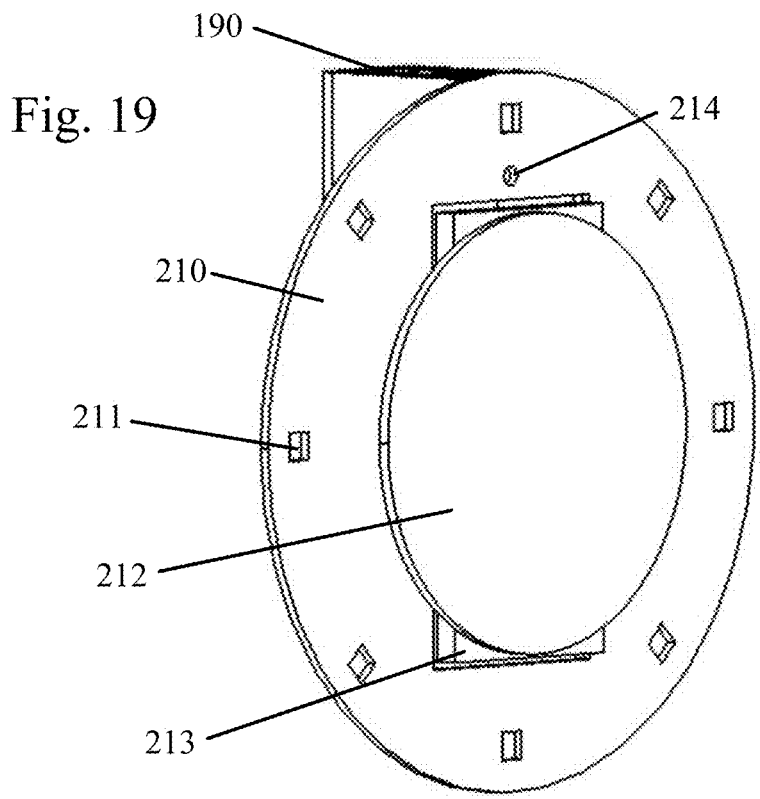
FIG. 19 shows a perspective view of a clamp and heat sink.

FIG. 19 shows a perspective view of a heat shield 210 of the clamp tube 190 with an array of bolt holes 211 around the edge to which the enclosure is secured. Heat sink block 213 draws heat from the cold side of the thermos-electric elements (not shown) beneath it. Heat sink radiator 212 is a wide thin plate to provide more surface area by which the natural airflow can draw off the heat more effectively. A spring 316 (not shown) presses down on the center of the heatsink elements 213, 212 to hold them tight to the heatsinks. Sample tube 314 passes through hole 214 to draw exhaust gas that collects inside of the clamp tube 190.

Figure 20:
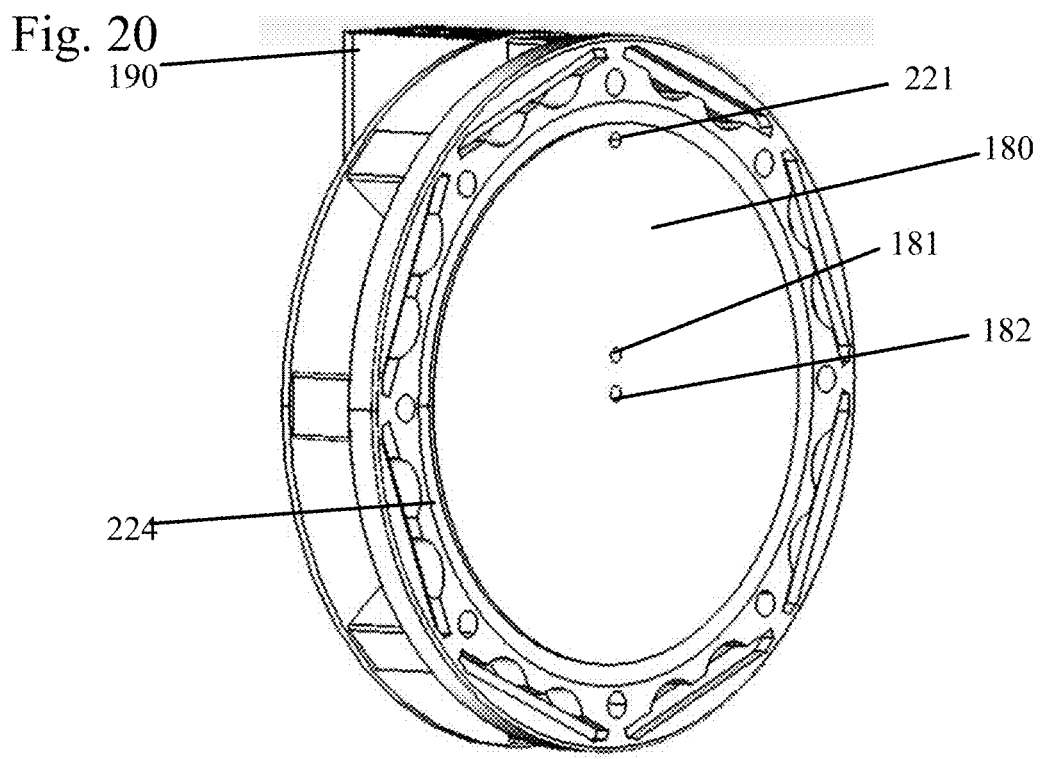
FIG. 20 shows a perspective view of a clamp heat sink and base.

FIG. 20 shows a perspective view of a clamp heat sink and base in enclosure base 180, hole 221 through which the exhaust sample gas is drawn into the enclosure inside of the sealing gasket that lays in the O-ring notch 224. Additional holes 222, 223 are present in face 220 of the clamp tube 190.

Figure 21:
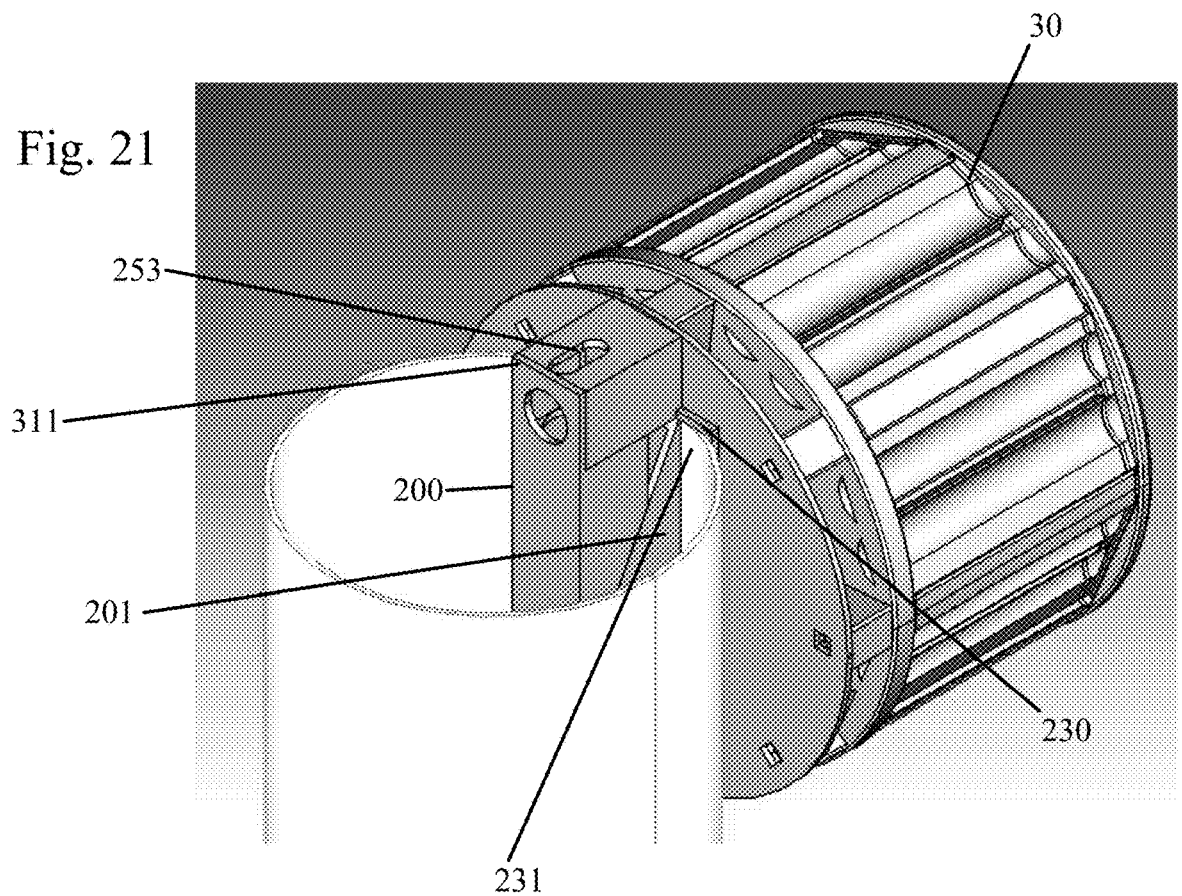
FIG. 21 shows a sensor unit attached by a clamp to a six-inch pipe.
Figure 22:
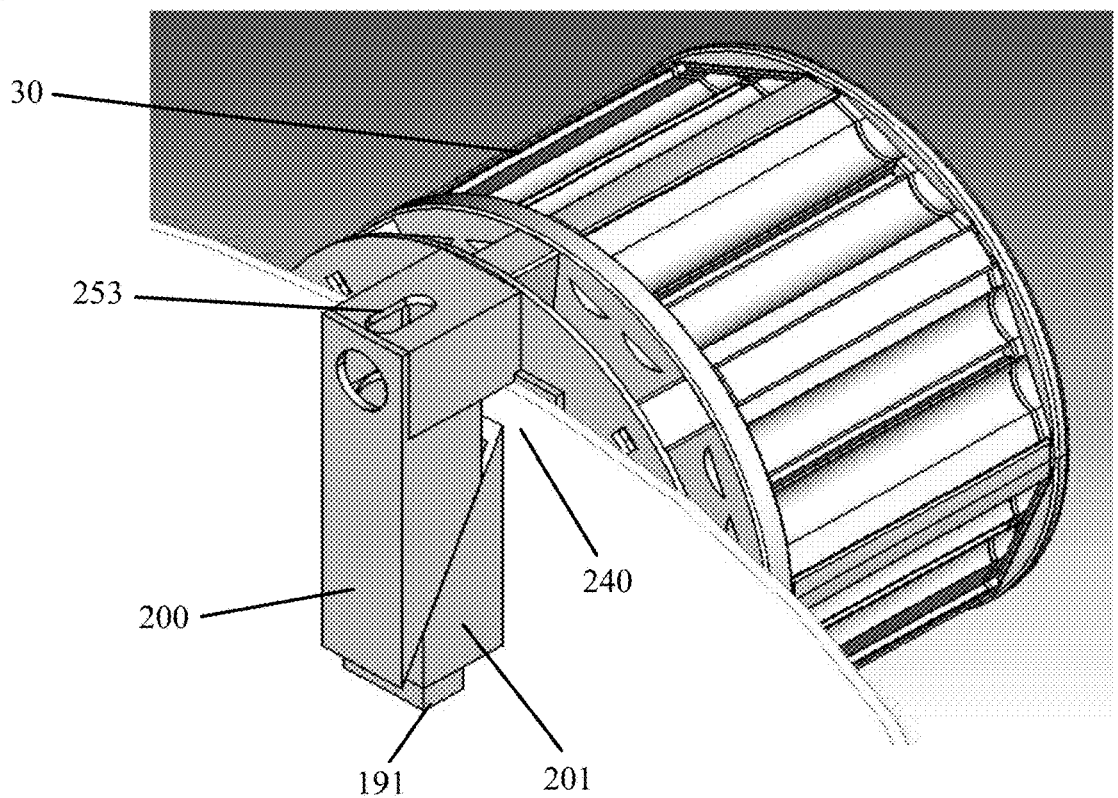
FIG. 22 shows a sensor unit attached by a clamp to a forty-inch pipe.

FIG. 21 shows an enclosure 30 with a sensor unit 10 attached by a mounting clamp 311 to a six-inch pipe. FIG. 22 shows an enclosure 30 with a sensor unit 10 attached by a clamp to a forty-inch pipe. FIGS. 21-22 show the clamp wedge 201 bearing down on the steel side of the exhaust pipe 230, 240 of differing diameters.

Figure 23:
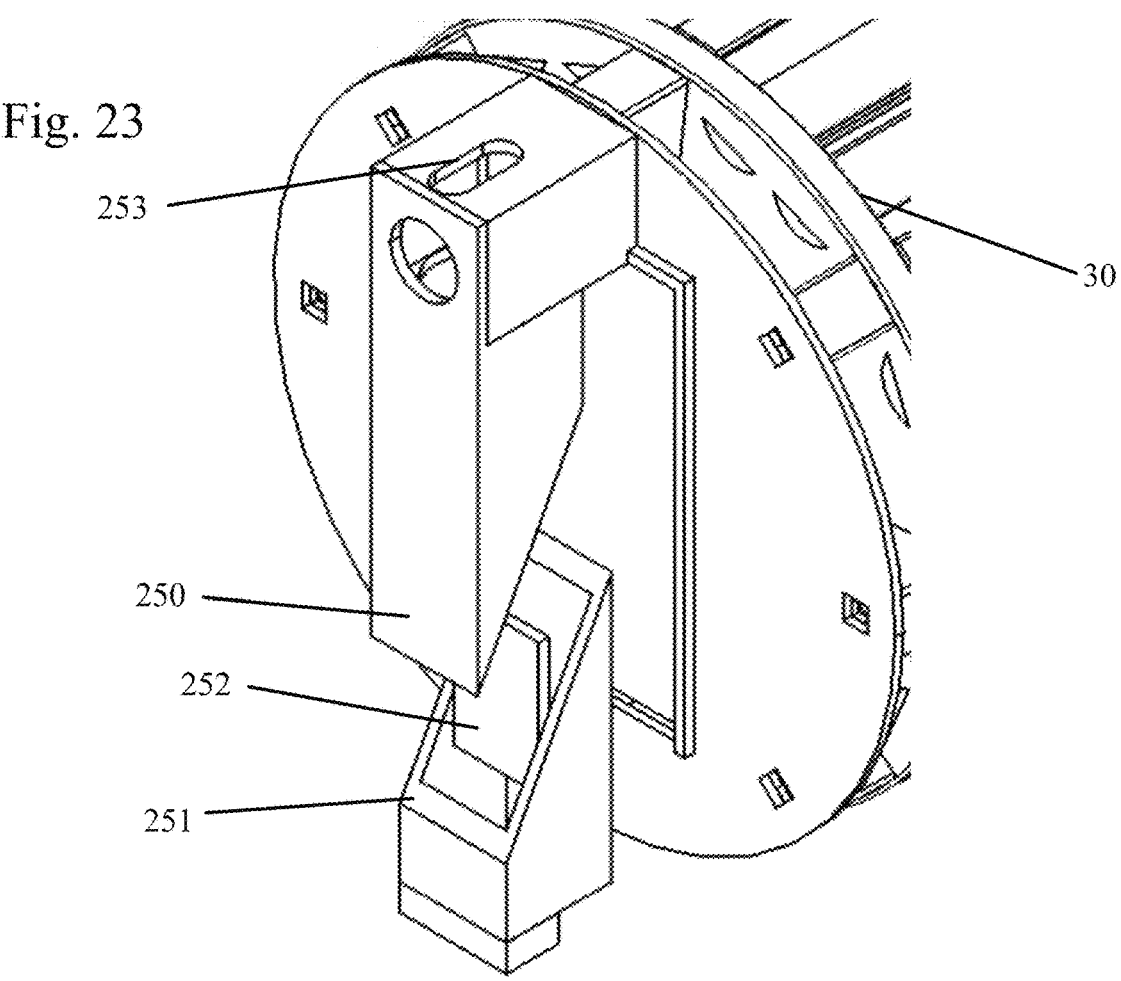
FIG. 23 shows a perspective view of a base of a sensor unit with a clamp.

FIG. 23 shows a perspective view of a base of an enclosure 30 with a clamp. As can be seen in this figure, a rectangular plate 252 inside the wedge of the clamp keeps the load bearing surfaces aligned under pressure. Rectangular plate 252 is affixed permanently to moveable wedge 251 and provides alignment for the load bearing edges between rigid element 250 and moveable wedge 251 without twisting. Slot 253 allows the bolt 312 to automatically adjust its location while the moveable wedge 251 moves during clamping relative to the rigid element 250.

Figure 24:
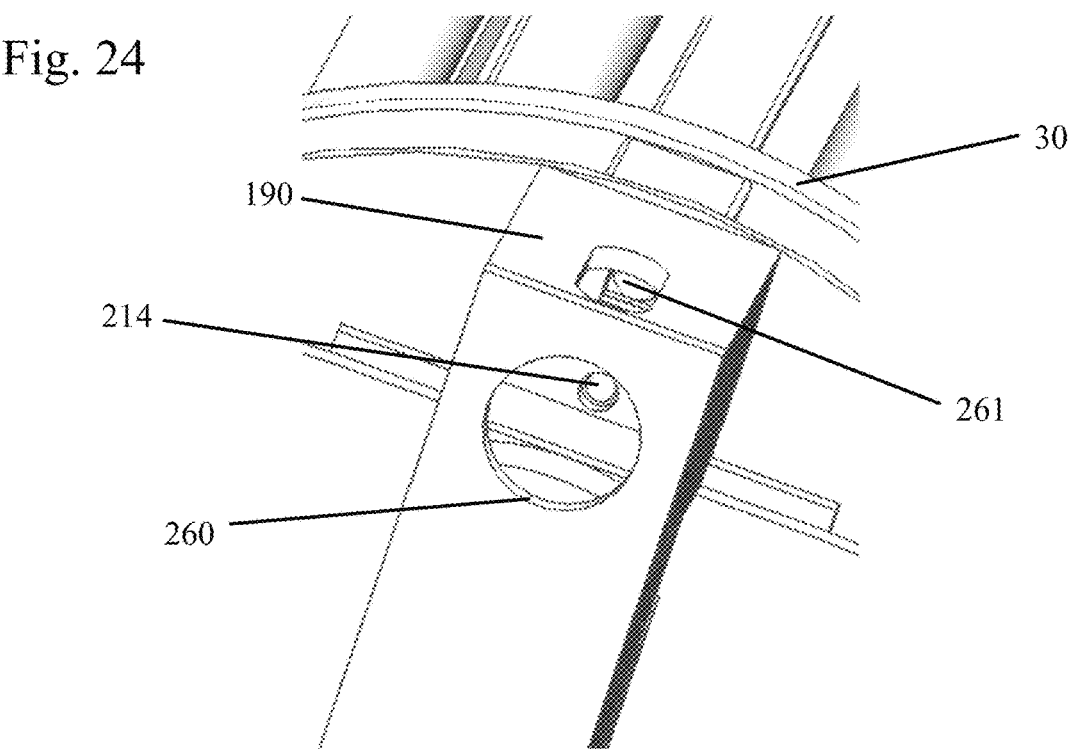
FIG. 24 shows a detail of a clamp on a pipe.
Figure 25:
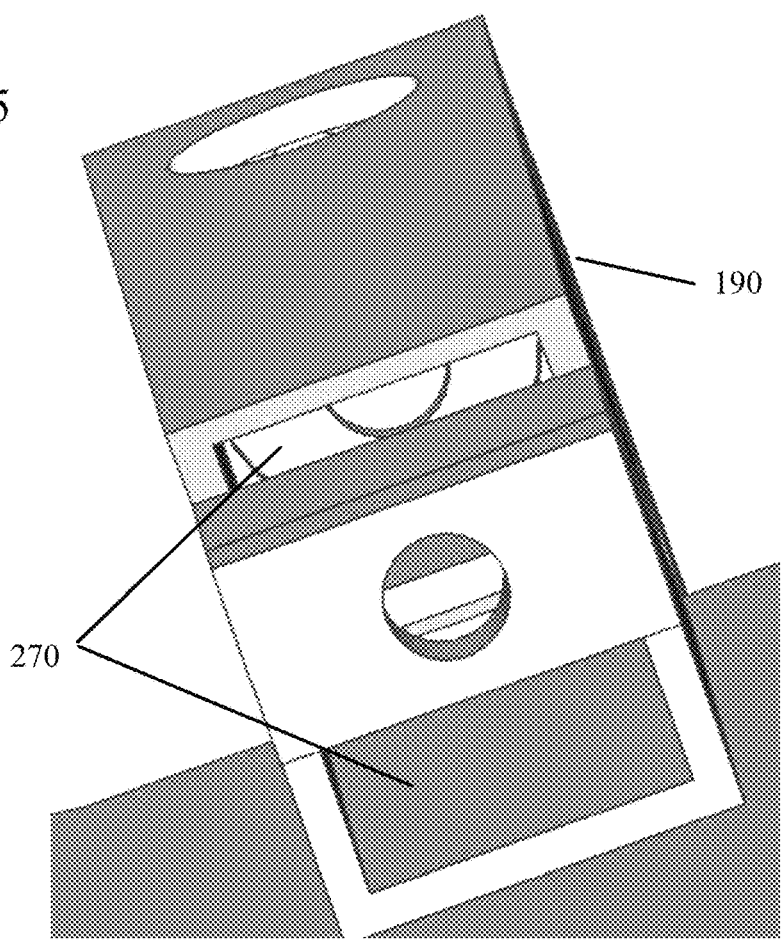
FIG. 25 shows a detail of a clamp on a pipe.
Figure 26:
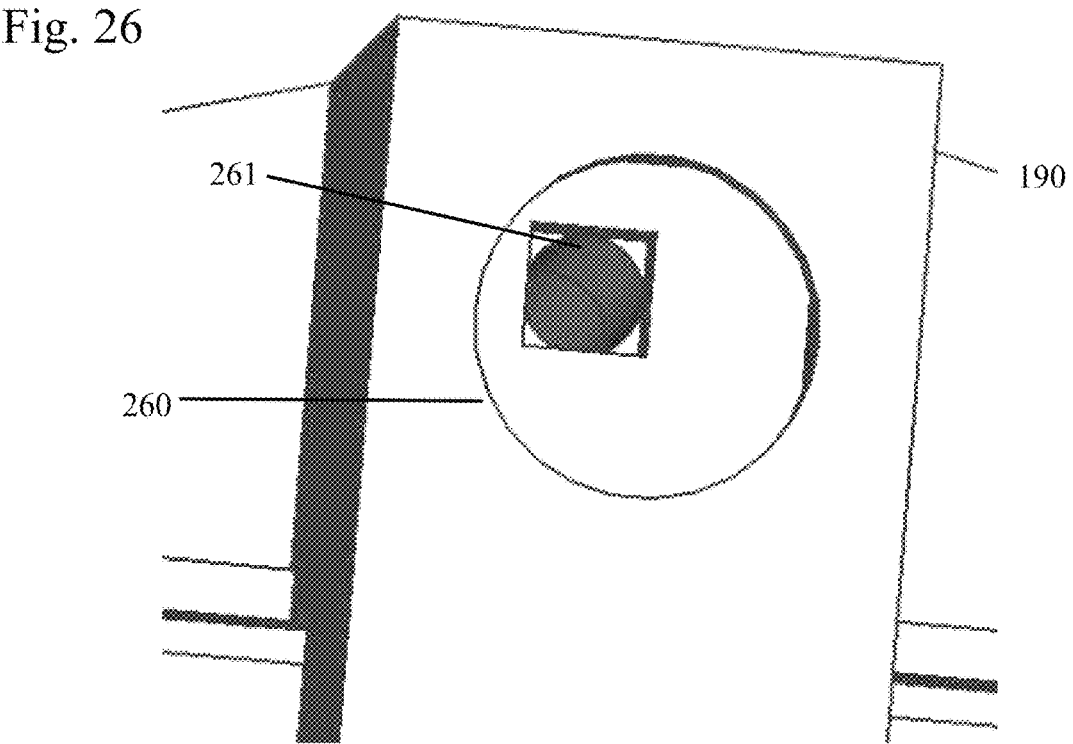
FIG. 26 shows a detail of the clamp.

FIGS. 24-26 shows a detail of a clamp on a pipe. Collection of exhaust gas through a tube passing through hole 214 from the space inside the tube 190 of the clamp is intentional to avoid direct exposure to heavy weather and the direct stream of the exhaust. It is intended to hold relatively steady a sample of exhaust from further in the exhaust pipe and reduce the impact of differing wind directions over the top of the pipe. The intake at the bottom of the clamp could be deliberately extended deeper into the pipe to collect a steadier sample of gas than collected by the clamp openings 270. Additionally, stainless steel filament pad may be used to fill inside of tube 190 and further buffer the exhaust sample from weather and soot. Bolt hole 261 and wider hole 260 accommodate the wide carriage bolt head during assembly.

Installation Options

Figure 12A:
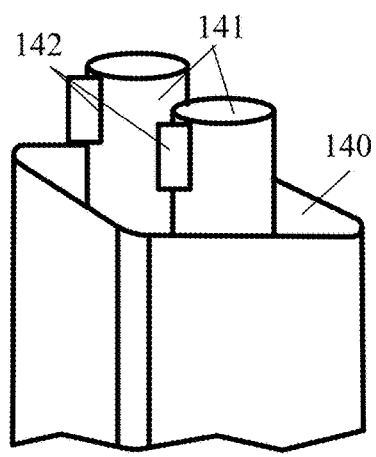
FIGS. 12a-12f show examples of alternative installation options.
Figure 12B:
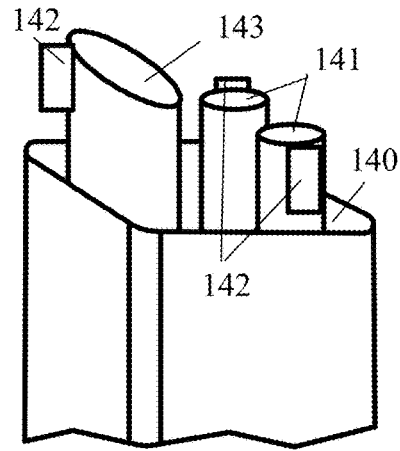
Figure 12C:
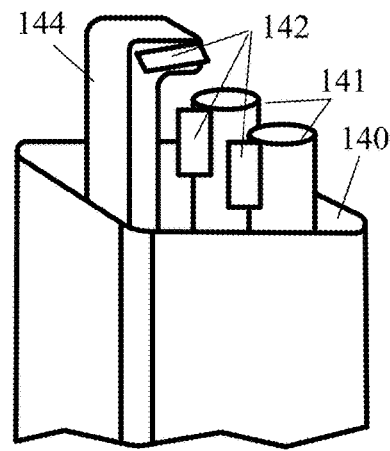
Figure 12D:
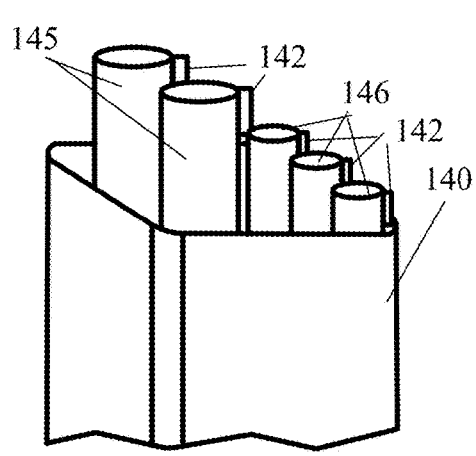
Figure 12E:
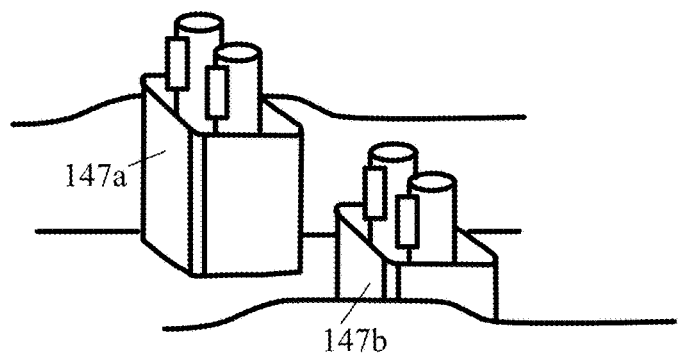

FIGS. 12a-12f show examples of alternative installation options. In FIGS. 12a-12d and 12f, there is a single funnel 140 within which there are multiple exhaust stacks 141, 143, 144, 145, and 146. FIG. 12e shows multiple funnels 147a and 147b of the sort shown in FIG. 12a. In each figure, locations 142 for installing sensor units 10 are indicated by boxes.

FIGS. 12a and 12e show a front mounting option, and FIG. 12d shows a back mounting option. A front or back install is more likely to occlude the antenna in the sensor unit with other pipes.

FIG. 12b shows an outboard side installation, which has a benefit of providing the same installation instructions for all installs.

FIG. 12c shows a ship which has a curved exhaust stack 144 in addition to two straight pipes 141. For curved pipes 144, a side mount 142 as shown would be preferred.

Figure 12F:
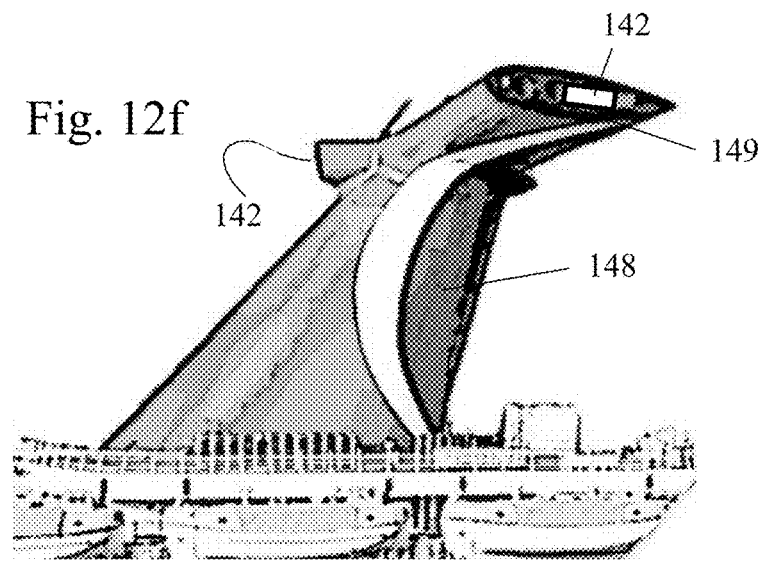

FIG. 12f shows a cruise ship funnel 148 of the design where multiple exhaust stacks 149 leave the funnel 148 horizontally at the ends of "wings".

Methods

Sampling Process

Low cost, low power $SO_2$ sensors do not have an adequately wide range to report the range of ppm values needed to do the calculations of $SO_2$ concentration in the exhaust to the accuracy required for the fuel sulfur compliance tests. Current regulations allow for 3.5% (35,000 ppm) $SO_2$ emission concentration for mid-ocean outside of SECA boundaries. On Jan. 1, 2020, that level is reduced to 0.5% (5000 ppm). Inside the SECA boundaries, near shore and ports, the limit is now, and will remain 0.1% (1000 ppm).

The maximum ppm range on low cost, low power $SO_2$ sensors which are commonly found available on the market is 2000 ppm. However, such sensors can still determine that some level of $SO_2$ is distinctly different from another.

The response to the series of very small exhaust gas samples across the element of the sensor is the salient data that can be used to characterize the $SO_2$ concentration in the exhaust gas. This can extend the total range of concentrations which can be identified. This process is generic, applicable to gas sensors with limited range, including both $SO_2$ and $CO_2$ sensors.

This response can be characterized in a number of ways:
number of sample pulses required to saturate the sensor, or read maximum value—higher concentrations have fewer sample pulses;
slope of the values of each pulse reading on the way to maximum—higher concentrations have steeper slope; and
elapsed time between sample start and maximum reading—higher concentrations have shorter time.

Some or all of these characterizations become inputs to the neural network, which is trained for classification and determining whether the sample is a high sulfur zone sample or low sulfur zone sample.

Low cost, low power $CO_2$ sensors may not reach saturation, but similar to the $SO_2$ sensor treatment, the pulse and slope may be the optimal method to condense and capture the salient characteristics. The $CO_2$ value corresponds to the amount of fuel burned for a given sample, and that could be used, as the IMO indicates, to determine percentage of sulfur in that amount of fuel. As an $SO_2$ value is incomplete and uncalibrated for each small pulse of a sample, one cannot determine the sulfur/fuel ratio with useful accuracy. Nonetheless, the $CO_2$ value is valuable for the same reason when integrated as an input into the neural network.

Wind Speed and Direction Integration

Watching for the pronounced change in readings of any of the internal sense chamber 40 will indicate that the length of the tube has been cleared of stale gas and a fresh sample has begun to enter the sense chamber 40. The count of small sample pulses to clear the intake tube can be used to realign the data from the air pressure sensors and to integrate wind speed and direction.

Neural Network Operation

There are interactive impacts of temperature, pressure, humidity, and voltage on the $SO_2$ and $CO_2$ sensor values.

Their datasheets indicate how to compensate, numerically, for these interactions to determine an accurate value after calibration.

Training a neural network with actual data automatically integrates these interactions. As production of the actual accurate numerical values for $SO_2$ and $CO_2$ is not required, this situation is preferred.

The neural network will have an input layer with nodes for each sensor value indicated earlier—including the $SO_2$ sensor response characteristics. There will be four outputs— (a) suspiciously low sulfur fuel; (b) valid low sulfur fuel; (c) valid higher sulfur fuel; and (d) egregiously high sulfur fuel.

Practically all samples may be assumed to be valid training data. Each new sample can be checked through the neural network to see if the expected result is returned for the current zone. If so, it will be assumed to be useful training data to tune the network connections. If the network training does not effectively resolve, it will be apparent during metadata analysis of all ship sensor data after sync with remote servers.

After each set of suitable new training sample data, the network will also be fed two additional fabricated sample sets that match the actual data except for the $SO_2$ readings— one with a suspiciously low $SO_2$/slope and high pulse count, and one egregiously high SO2/slope and low pulse count. This will provide the four-tier classification output for which the neural network is configured. Ships or vessels may or may not comply with International Maritime law which requires their use of compliant fuels, but the system will be detecting that they are switching in a compliant manner.

Non-Sensor Data Inputs

There will be an input node to receive the sulfur concentration in the fuel. An automatic feed of this particular data is not necessary. Alternatively, the system could default to a minimally compliant value. This is a reasonable assumption because there is a strong financial disincentive to buy exceedingly compliant fuel. Relying on an assumption of compliance with maritime law provides an advantage of being able to predict the minimal compliance.

Data Integrity

The data read by the sensor unit 10 is captured immediately in the immutable block chain record of a distributed version control system. This is preferably a system such as the proven open-source Fossil version control system.

When each of the sensor units 10 are able, they push all of their data up to remote servers where ship-wide and fleet-wide analysis can be done.

As future data comes in to the remote servers, the system will count on compliance of the environment given to test. If sensor units 10 provide values that no longer classify, the system will receive data that is unrecognized and ineffective at training the network. If this happens, one can assume one of the sensor units 10 is invalid. If all of the sensor units 10 provide unexpected values, it can be assumed that the sensor unit 10 has either been tampered with or the electronics or case is damaged. Any of these situations warrant investigation and remediation.

User Interface

Figure 10:
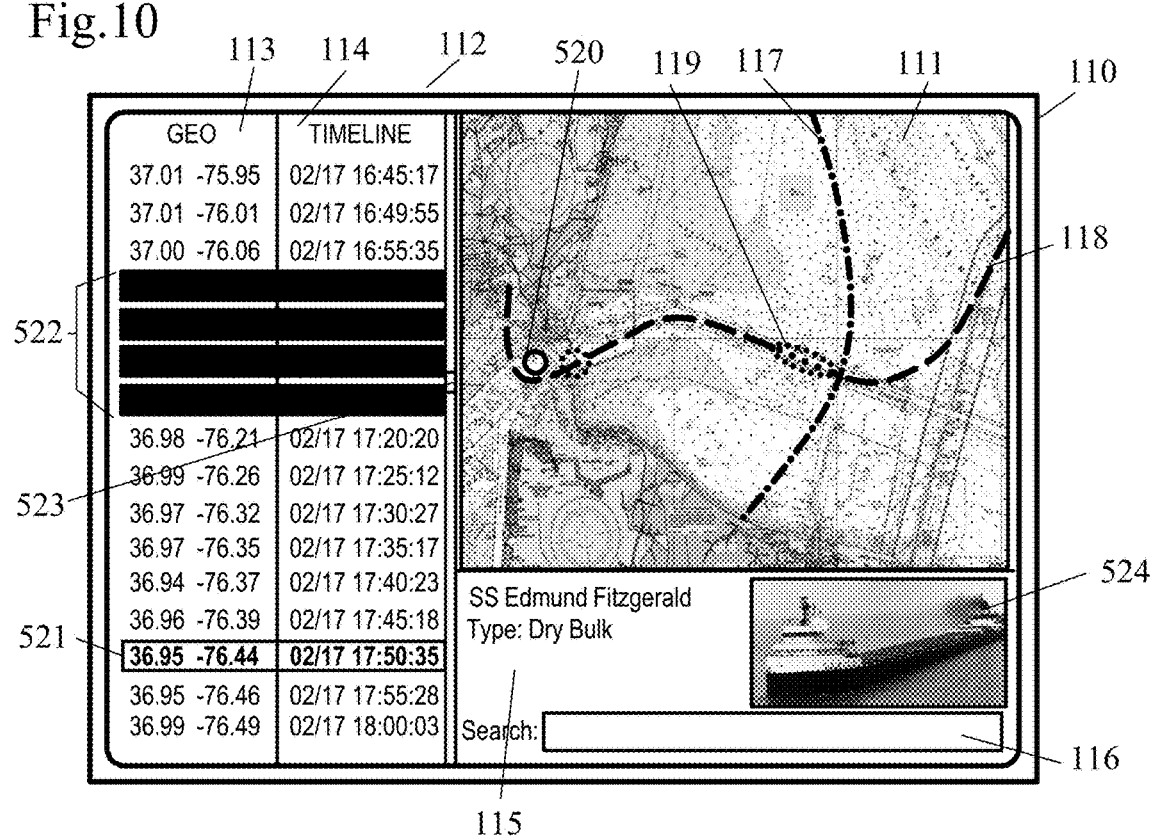
FIG. 10 shows an example of a user interface to convey ship data to client.

FIG. 10 shows an example user interface concept to convey ship data to a client. The display may be implemented on any hardware desired, such as a tablet display 110 as shown in the figure. The example display in the figure is divided up into a time-data section 112, which has a column for geographic location (lat/lon) 113 and for time 114. A scroll bar 523 can be provided to give easy navigation through the table in a manner common to the art. An identification section 115 can be provided to display information about the identity of the vessel, which may include a picture 524 and other information, such as the "Type: Dry Bulk" note on the example display. A search box 116 may also be provided.

A map display 111 shows the path 118 of the vessel during the time interval shown on the time-data section 112. One of the time-data entries 521 is selected, and the location of the vessel on its path 118 at that time is shown by a circle 520 on the map.

The map also indicates the boundary of the SECA by a dash-dot line 117. Vessels inbound to the port are required to switch to a low-sulfur fuel before crossing the boundary of the SECA 117.

In this example, the vessel was late in switching fuels. During the time that the vessel was in the dotted portion 119 of the course line 118, it was still burning high-sulfur, which means the vessel was out of compliance during this period. The entries 522 on the time-data display 112 which correspond to this out-of-compliance period are highlighted to show the occurrence of the violation.

Sampling Strategy

Figure 11:
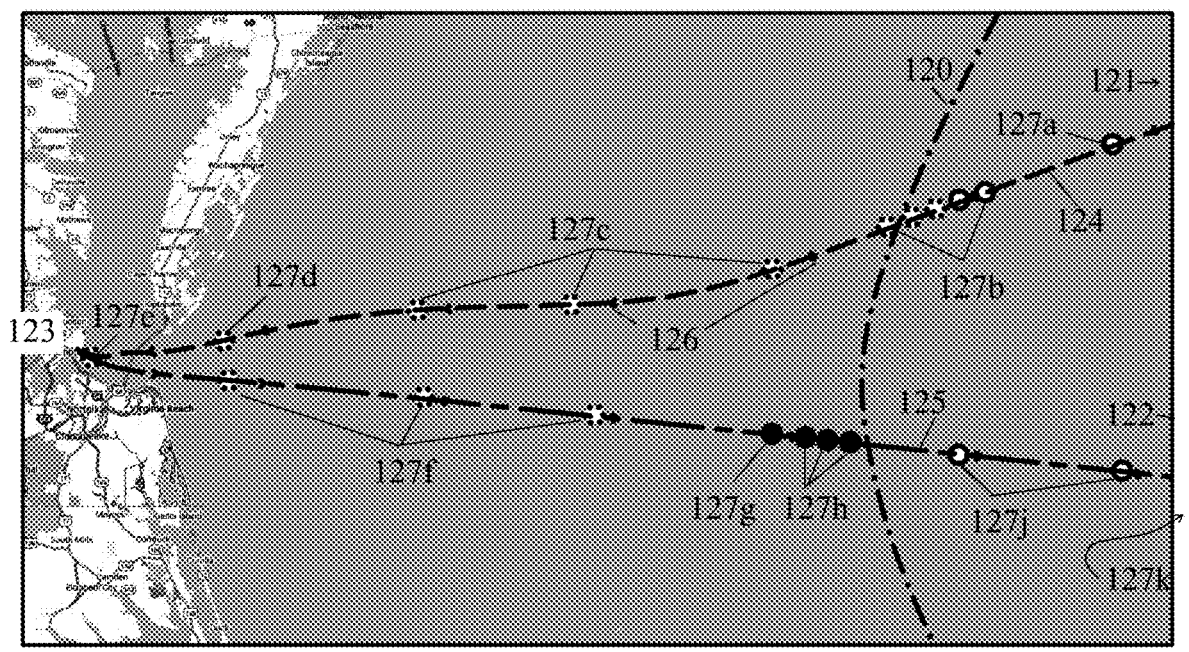
FIG. 11 shows a sketch of a sample strategy as a ship crosses a SECA boundary.

FIG. 11 shows a sketch of a sample strategy as a ship crosses a SECA boundary (dash-dot line 120) from out at sea 121 to port 123 and back to sea 122. The inbound path of the ship is represented by dashed line 124, and the outbound path of the ship is represented by short-long dash line 125. Each arrow 126 on each of the paths 124 and 125 represents approximately an hour's sailing.

The circles 127a-127j along the paths 124 and 125 represent the point at which the system takes action, which will be explained in detail in the following description. The black-filled circles 127g-127h represent readings which are out of range or "bad" (i.e. noncompliant), while the open (white-filled) circles 127a-127f and 127j indicate readings which are within range (i.e. compliant). Circles with dotted lines show low-emissions readings, circles with solid lines show high-emissions readings.

The exemplary strategy proceeds as follows, with the numbers referring to points on FIG. 11:

127a—At this point, the ship is outside the SECA boundary 120 on the inbound path 124, so high sulfur fuel is permitted. The readings from the sensor units 10 would be high, but still compliant, since at this point the more restricted range of the SECA does not yet apply. The system takes readings on a selected schedule, for example every hour as shown on FIG. 11. More frequent or less frequent schedules could also be chosen as appropriate. When a reading is taken, the data from the reading—for example, time, location, compliance status, and perhaps raw sensor data numbers—are stored in a repository on the ship for later transmission to the central server on shore.

127b—The ship is approaching the SECA boundary 120. The system starts taking more frequent readings, perhaps every ten minutes or more frequently, so as to capture the data showing a switch from high sulfur fuel to low sulfur fuel.

127c—The ship switched to low sulfur fuel as required, and the system confirms this with readings which show emissions to be compliant.

127d—At this point the ship is within range of the shore-based mobile telephone network. The system connects to the network and transmits a status report to the server at least indicating that the onboard system is operating OK and the ship is compliant. If desired, a full upload of data from the onboard repository could be transmitted to the central server at this time.

127e—The ship is in port 123. The system continues to monitor emissions to make sure it remains compliant. If it did not do so in step 127d, the data in the repository can be uploaded to the central server at this time while the ship is in port.

127f—The ship has left port by outbound path 125. The readings show that the emissions remain compliant with the inside-SECA standards.

127g—The system has detected a sample with a "bad" or out-of-range reading. It is possible that the ship has changed over to high sulfur fuel too soon, outside the SECA boundary 120, or this might be a spurious reading caused by a bad sample or transient condition.

127h—The system takes more frequent readings for a period, in order to confirm that the sample actually shows an uncompliant status, and is not based on spurious readings. The readings continue to be out of range, so the system logs this as a noncompliant situation.

127j—Since the ship is outside the SECA boundary 120, the system would be applying the higher range. The readings taken by the system are once again "good", indicating the ship is compliant with the standards applicable to this area.

127k—When the ship reaches its next port (off the map), all of the historical data accumulated since the last upload is transmitted from the onboard repository to the central server.

Alerts can be sent to a user on the ship with the sensor units or an enforcement or government agency regarding compliance or non-compliance.

Decision Tree

Figure 15:
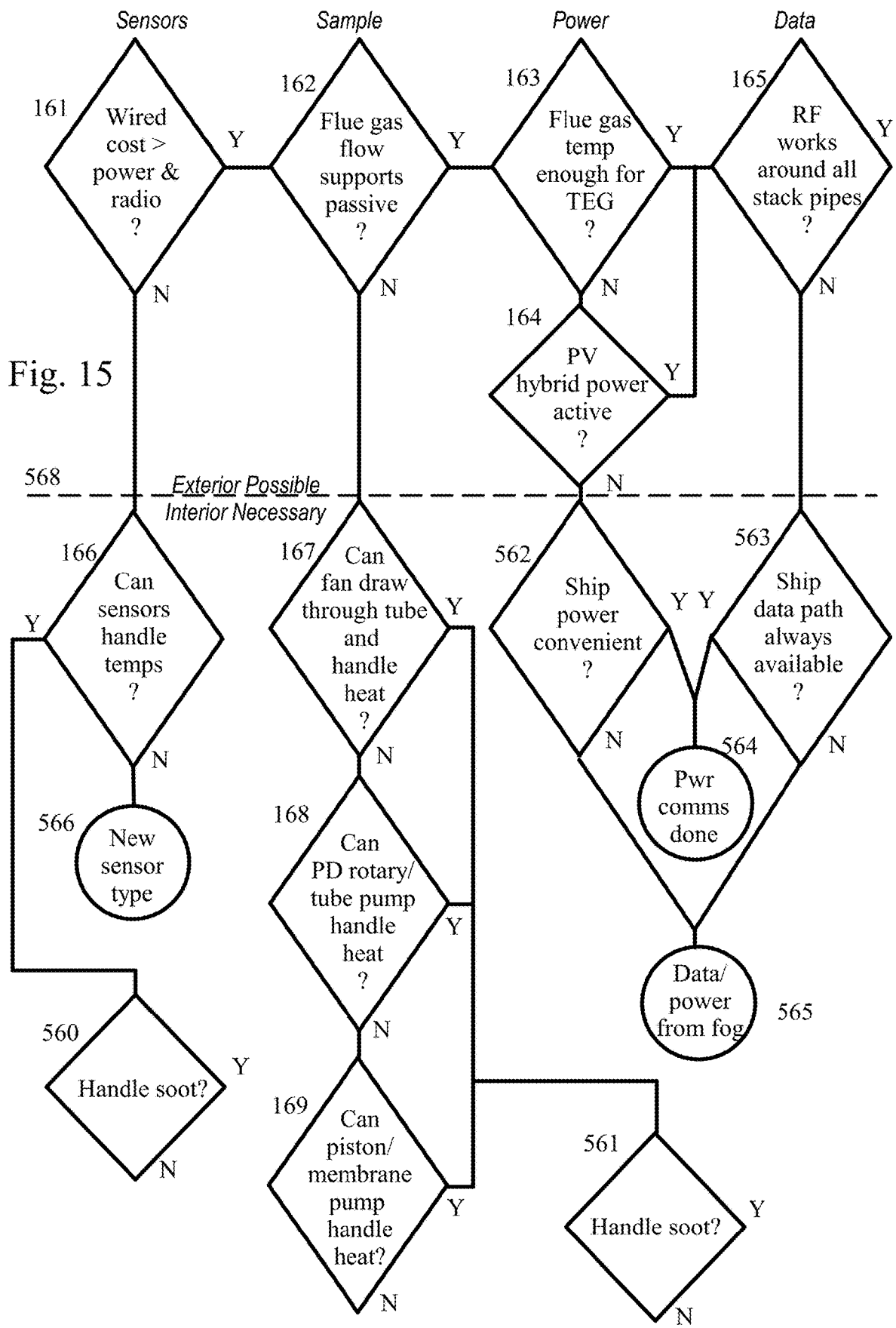
FIG. 15 shows a decision tree.

FIG. 15 shows a decision tree deciding where to install a sensor unit and power and communication options. The decisions above line 568 refer to situations where exterior solutions are possible, decisions under line 568 refer to situations which require interior solutions. The decision tree is divided into four vertical columns, dealing with Sensors, Sampling, Power and Data, respectfully. Taking each of these in turn:

Sensors:
161—Does a wired installation cost more than one using power and radio? If so, then move on to Sampling, step 162. If not, then go to step 166.
166—Can sensors handle the temperatures? If they cannot, then go to step 566 and choose a new sensor type. If they can, proceed to step 560.
560—Can the sensors handle soot? This decision block can lead to additional processing, as might be determined later.

Sampling:
162—Is the flow of gas in the flue fast enough to support passive sampling designs? If so, move on to Power, step 163. If not, proceed to step 167.
167—Can a fan draw through a narrow tube and handle the heat? If so, then proceed to step 561. If not, go on to step 168.
168—Can a positive displacement rotary or tube pump handle the heat? If so, proceed to step 561. If not, go on to step 169.
169—Can a piston or membrane pump handle the heat? If so, proceed to step 561. If not, this decision block can lead to additional processing, as might be determined later.
561—Can the sensors handle soot? This decision block can lead to additional processing, as might be determined later.

Power:
163—Is the flue gas temperature high enough to drive a Thermo Electric Generator (TEG)? If so, move on to Data, step 165
164—Can Photovoltaic (PV) hybrid power active designs? If so, move on to Data, step 165. If not, proceed to step 562
562—Is ship power always convenient? If so, then move on to step 564. If not, proceed to step 565. It should be noted that initial testing has found neither power or communications channels were consistently or easily provided where needed, and that self power was preferable to avoid the cost/effort of custom integration on every installation.

Data:
165—Will RF work around all stack pipes? If not, then proceed to step 563.
563—Is ship data path always available? If so, then move on to step 564. If not, proceed to step 565. As with step 562, it should be noted that initial testing has found neither power or communications channels were consistently or easily provided where needed, and that self power was preferable to avoid the cost/effort of custom integration on every installation.

Accordingly, it is to be understood that the embodiments of the invention herein described are merely illustrative of the application of the principles of the invention. Reference herein to details of the illustrated embodiments is not intended to limit the scope of the claims which will be filed in a utility patent application claiming benefit from this provisional application, which themselves will recite those features regarded as essential to the invention.

What is claimed is:

1. A method of installing a sensor unit to test for a level of sulfur dioxide in exhaust gas of a ship comprising:
for each stack of the ship with an opening facing upwards, mounting a sensor unit on an outboard side of the stack to measure for at least the level of sulfur dioxide,
wherein the sensor unit comprises an enclosure pump block housing defining a sensor chamber containing a sensor for sensing at least sulfur dioxide levels in the exhaust gas; a sample pump within the enclosure pump block housing for pumping exhaust gases into the sensor chamber; a purge pump within the enclosure pump block housing for pumping exhaust gases out of the sensor chamber; and a first filter and a second filter each with a thermally conductive surface to condense moisture present within the exhaust gases which is collected in a chamber surrounding each of the first filter and the second filter and defined by the enclosure pump block housing, the chamber surrounding each of the first filter and the second filter having a hole connected to outside of the enclosure pump block housing to discharge collected condensed moisture;

wherein the exhaust gas of the exhaust pipe is drawn into the sensor chamber through the first filter by the sample pump, with sulfur dioxide sensed within the sensor chamber and pumped out of the sensor chamber by the purge pump, pulling external displacement air through the second filter.

2. A sensor unit for sampling exhaust gas from a stack within a single funnel of a ship comprising:
an enclosure pump block housing defining a sensor chamber containing a sensor for sensing at least sulfur dioxide levels in the exhaust gas;
a sample pump within the enclosure pump block housing for pumping exhaust gases into the sensor chamber;
a purge pump within the enclosure pump block housing for pumping exhaust gases out of the sensor chamber; and
a first filter and a second filter each with a thermally conductive surface to condense moisture present within the exhaust gases which is collected in a chamber surrounding each of the first filter and the second filter and defined by the enclosure pump block housing, the chamber surrounding each of the first filter and the second filter having a hole connected to outside of the enclosure pump block housing to discharge collected condensed moisture;
wherein the exhaust gas of the exhaust pipe is drawn into the sensor chamber through the first filter by the sample pump, with sulfur dioxide sensed within the sensor chamber and pumped out of the sensor chamber by the purge pump, pulling external displacement air through the second filter.

3. The sensor unit of claim 2, wherein the sensor is controlled by a microcontroller which receives power via a solar energy source or thermoelectric energy source.

4. The sensor unit of claim 2, wherein the enclosure pump block housing is received within an enclosure comprising: a mounting base, a cylindrical middle and a dome top fastened together via bolts around a perimeter of the dome top passing through the dome top, the cylindrical middle and engaging with the mounting base, wherein the cylindrical middle includes a plurality of photovoltaic modules and at least one circular photovoltaic module in the dome top.

5. The sensor unit of claim 4, wherein in between the plurality of photovoltaic modules of the cylindrical middle are airflow channels.

6. The sensor unit of claim 4, wherein in between the cylindrical middle and the mounting base is a heat shield adjacent the cylindrical middle and a mounting surface adjacent the mounting base separated from the heat shield by standoffs.

7. The sensor unit of claim 6, wherein the standoffs are configured to direct air towards a center of the enclosure to cool a cold side of the heat shield and a thermoelectric generator.

8. The sensor unit of claim 6, wherein a surface of the heat shield adjacent the cylindrical middle includes a plurality of vent fins.

9. The sensor unit of claim 4, wherein an internal diameter of the cylindrical middle includes slots for receiving circuit boards associated with the sensor.

10. The sensor unit of claim 5, wherein placed between photovoltaic modules and airflow channels are weep holes passing from an outside surface to an internal diameter of the cylindrical middle.

11. The sensor unit of claim 6, wherein the mounting base of the enclosure further comprises a flange for centering a spring between the mounting base and heat shield.

12. The sensor unit of claim 4, further comprising a mounting clamp attached to the mounting base and the heat shield.

13. The sensor unit of claim 12, wherein the mounting clamp comprises a tube having a slot on a top surface for receiving a bolt which extends a length and threads into a block, the block being attached to a moveable wedge, and a rigid element connected to the top surface, wherein threaded engagement of the bolt with the block moves the wedge relative to the rigid element and slides the bolt within the slot and the wedge towards the mounting base to clamp to a pipe edge of the stacks relative to the mounting base.

14. The sensor unit of claim 12, wherein a sample of the exhaust gas pumped into the sensor chamber is collected from within the mounting clamp.

15. The sensor unit of claim 2, wherein the sensor unit is mounted to an outboard side of at least one stack of a plurality of stacks within the single funnel.

16. A method of sampling exhaust gas produced by fuel burned by a ship from a funnel of the ship using sensor units comprising an enclosure pump block housing defining a sensor chamber containing a sensor for sensing at least sulfur dioxide levels in the exhaust gas; a sample pump within the enclosure pump block housing for pumping exhaust gases into the sensor chamber; a purge pump within the enclosure pump block housing for pumping exhaust gases out of the sensor chamber; and a first filter and a second filter each with a thermally conductive surface to condense moisture present within the exhaust gases which is collected in a chamber surrounding each of the first filter and the second filter and defined by the enclosure pump block housing, the chamber surrounding each of the first filter and the second filter having a hole connected to outside of the enclosure pump block housing to discharge collected condensed moisture; wherein the exhaust gas of the exhaust pipe is drawn into the sensor chamber through the first filter by the sample pump, with sulfur dioxide sensed within the sensor chamber and pumped out of the sensor chamber by the purge pump, pulling external displacement air through the second filter, the method comprising:
sensing sulfur dioxide levels within the exhaust gas on a selected schedule of sensor readings per a time period by the sensor units and corresponding the sensed sulfur dioxide levels with at least: time, geographic location and compliance status to generate emissions data;
determining a geographic location of the ship inbound relative to a sulfur emission control area is within a designated range and increasing a number of sensor readings within the time period; and
determining the ship is within a range of a telecommunications network at a port and sending a report regarding sulfur dioxide levels in fuel burned by the ship based on the location of the ship, wherein when sulfur dioxide levels are above a threshold within the sulfur emission control area, sending an alert to a user.

17. The method of claim 16, wherein the user is a user on the ship.

18. The method of claim 16, wherein the user is an enforcement agency.

19. The method of claim 16, wherein the emissions data associated with sulfur dioxide levels is stored in blockchain.

20. The method of claim 19, wherein compliance of the fuel burned by the ship represented by the emissions data relative to the sulfur emission control area is determined by a neural network.

* * * * *